United States Patent
Knuckley et al.

(10) Patent No.: US 12,358,867 B1
(45) Date of Patent: Jul. 15, 2025

(54) PEPTOID-BASED INHIBITORS OF THE PROTEIN ARGININE METHYLTRANSFERASE (PRMT) FAMILY

(71) Applicants: Bryan Knuckley, Jacksonville, FL (US); Corey P. Causey, Jacksonville, FL (US); Fatima Khwaja Rehman, Jacksonville, FL (US)

(72) Inventors: Bryan Knuckley, Jacksonville, FL (US); Corey P. Causey, Jacksonville, FL (US); Fatima Khwaja Rehman, Jacksonville, FL (US)

(73) Assignee: University of North Florida Board of Trustees, Jacksonville, FL (US)

( * ) Notice: Subject to any disclaimer, the term of this patent is extended or adjusted under 35 U.S.C. 154(b) by 0 days.

(21) Appl. No.: 18/643,330

(22) Filed: Apr. 23, 2024

Related U.S. Application Data

(62) Division of application No. 17/527,475, filed on Nov. 16, 2021, now Pat. No. 11,993,556.

(60) Provisional application No. 63/114,813, filed on Nov. 17, 2020.

(51) Int. Cl.
*C07C 259/06* (2006.01)

(52) U.S. Cl.
CPC .................... *C07C 259/06* (2013.01)

(58) Field of Classification Search
CPC ..................................... C07C 259/06
See application file for complete search history.

(56) References Cited

U.S. PATENT DOCUMENTS 11,993,556 B1 * 5/2024 Knuckley ............. C07C 259/06

OTHER PUBLICATIONS

Kong et al., Selective small-chemical inhibitors of protein arginine methyltransferase 5 with anti-lung cancer activity. PLoS ONE 12(8): e0181601. https://doi.org/1031371/journal.pone.0181601, 2017.*

* cited by examiner

*Primary Examiner* — Sun Jae Yoo
(74) *Attorney, Agent, or Firm* — Michele L. Lawson; Smith & Hopen, P.A.

(57) ABSTRACT

Novel peptoid compounds, compositions and methods of using the compounds and compositions to inhibit protein arginine methyltransferase (PRMT) and induce apoptosis in cancer cells are presented.

5 Claims, 20 Drawing Sheets

Figure 5A-B

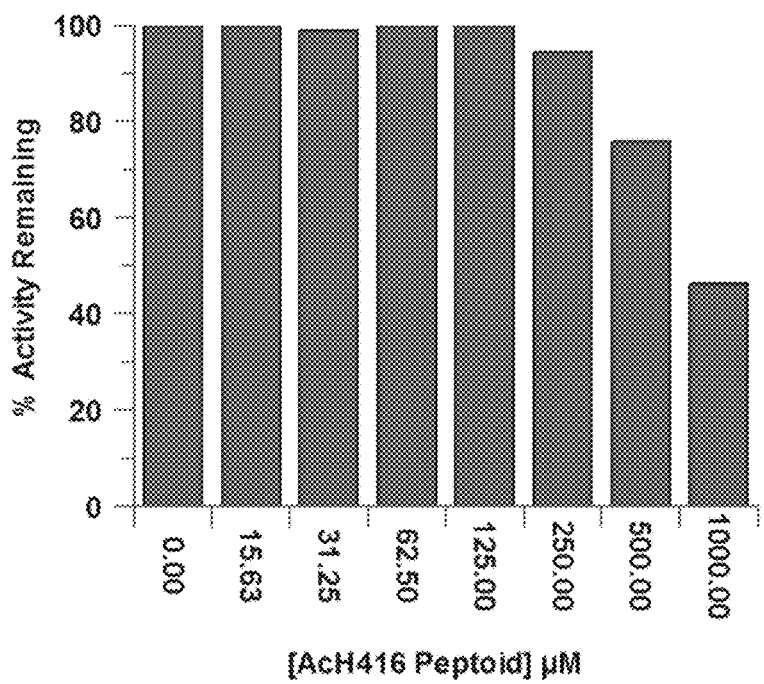
Figure 6
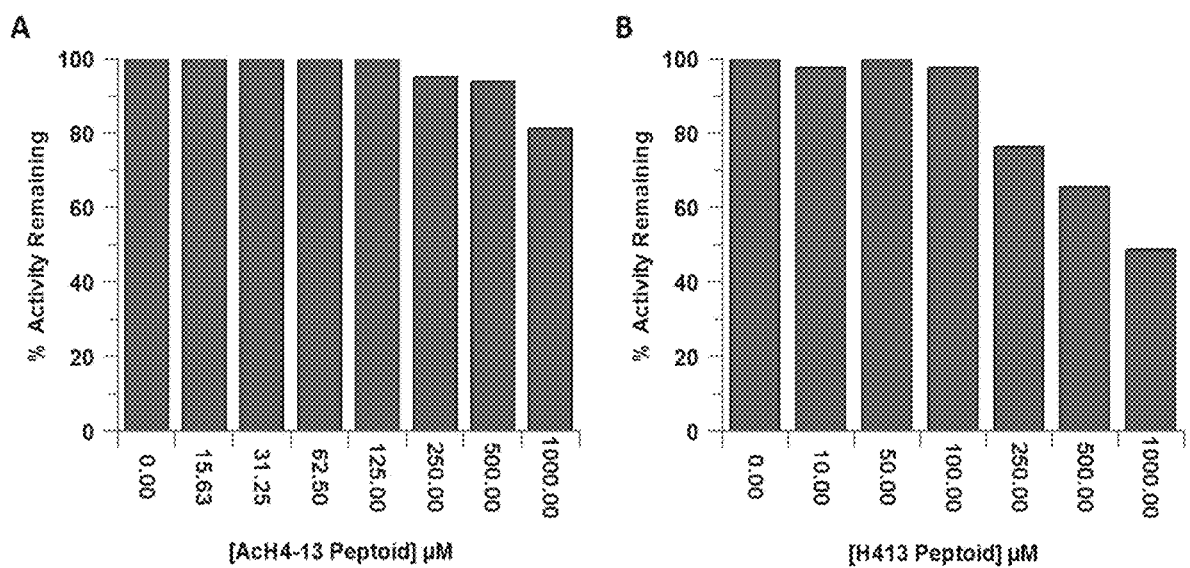
Figure 7A-B

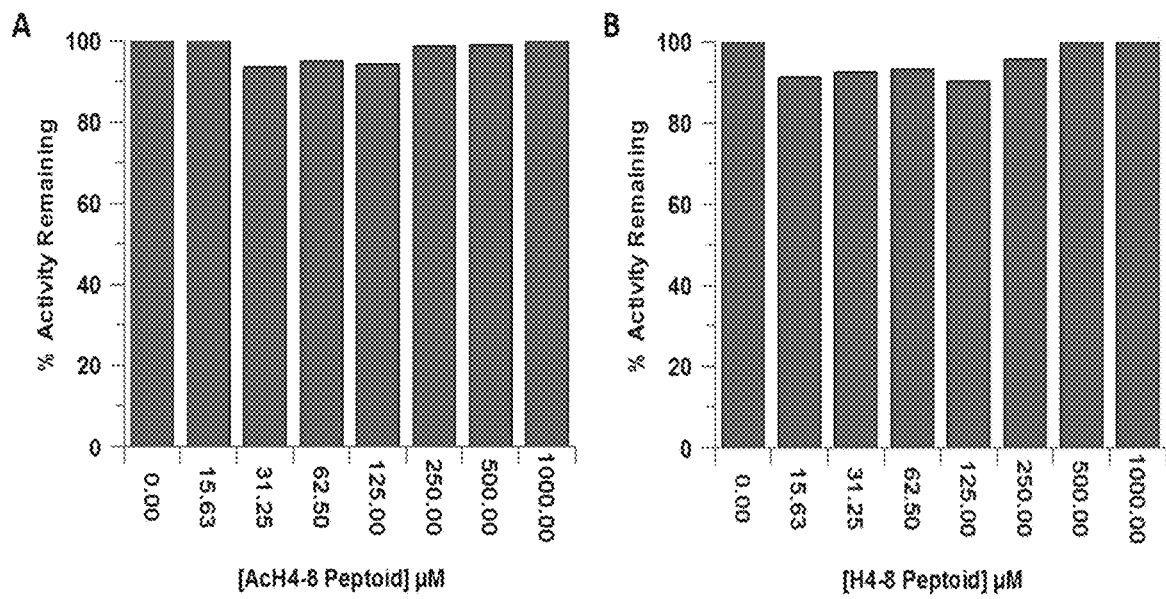
Figure 8A-B
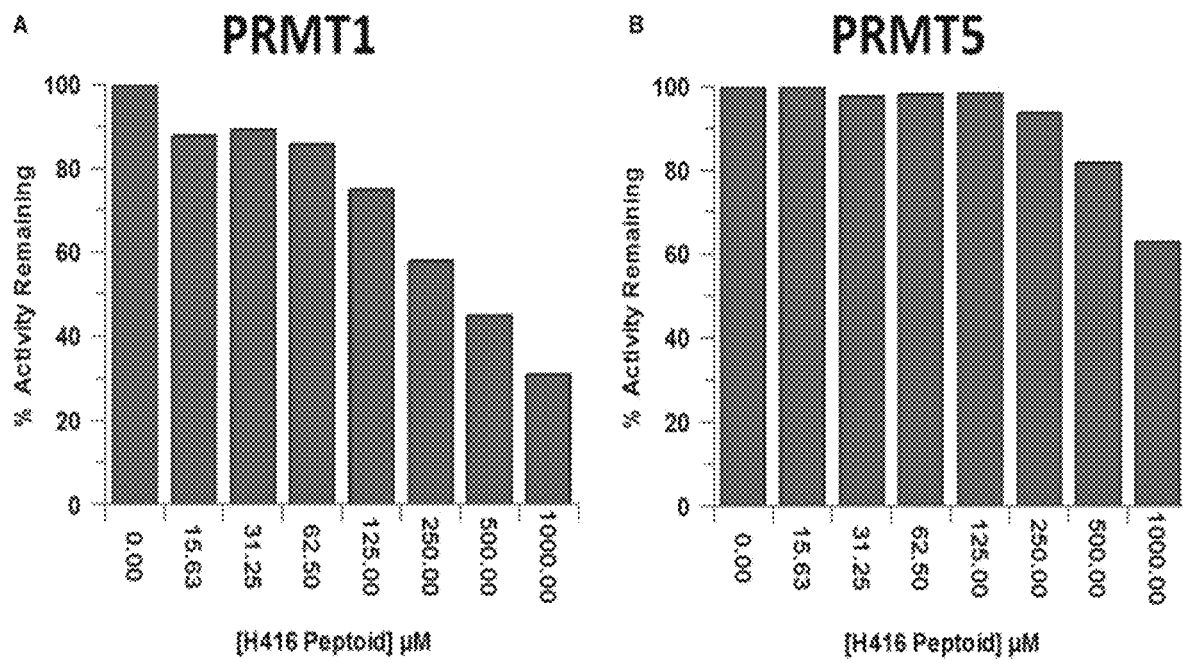
Figure 9A-B

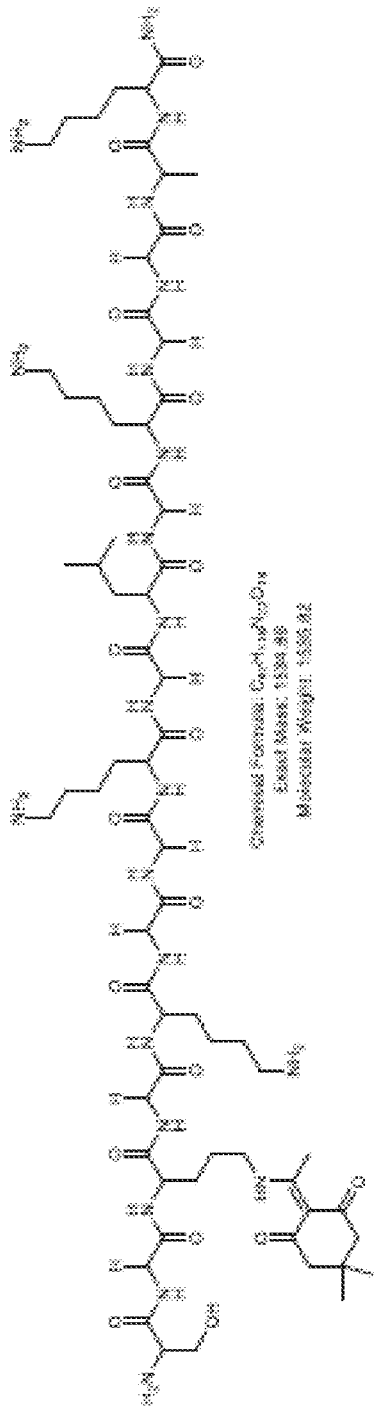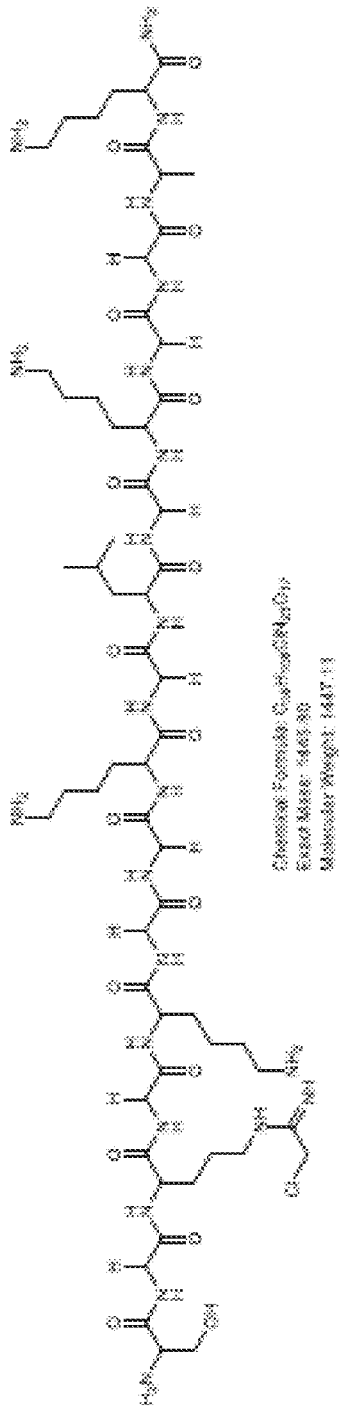
FIG. 11

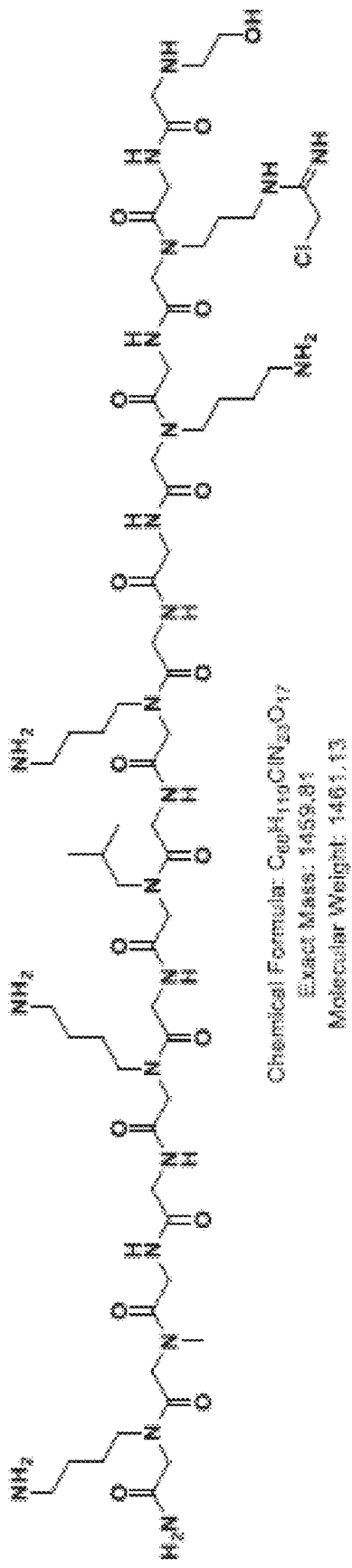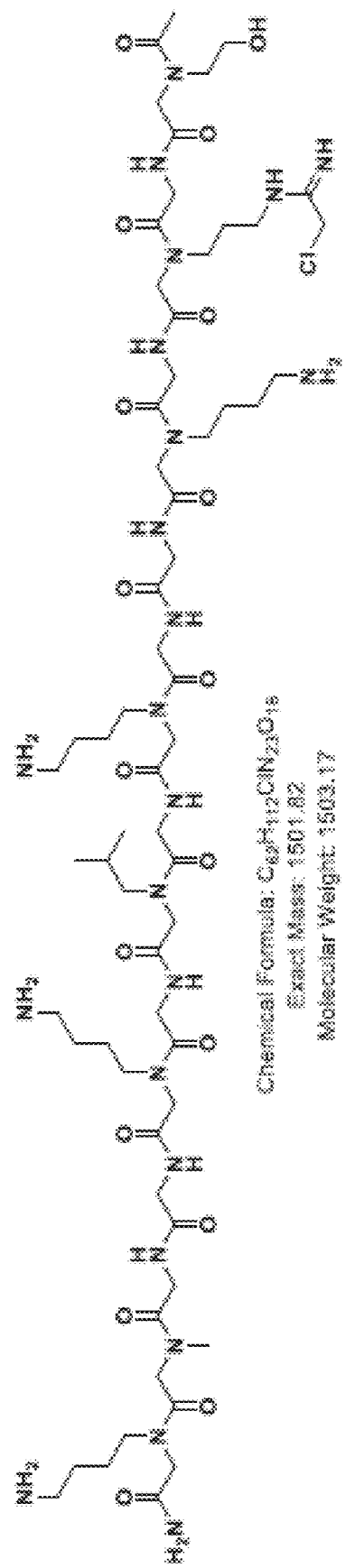
FIG. 15

A.
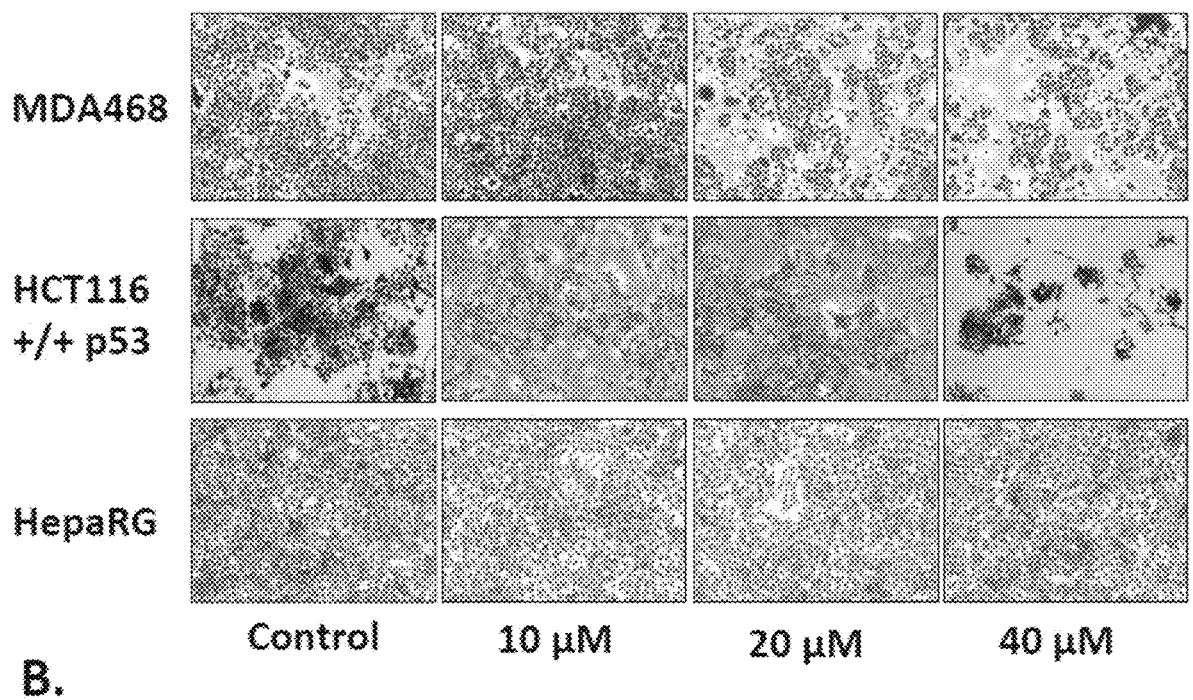
B.
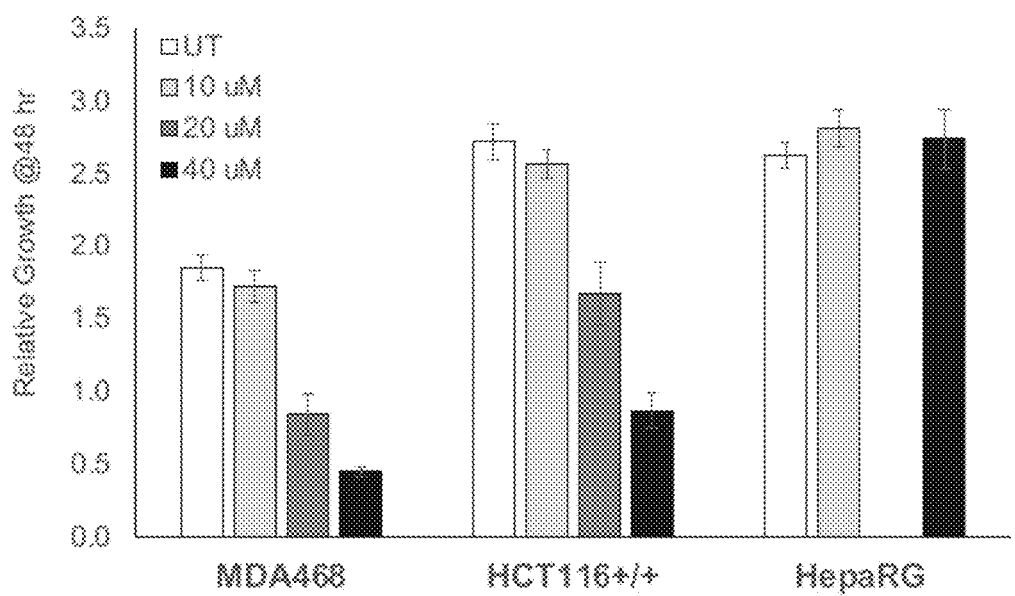
FIG. 19A-B

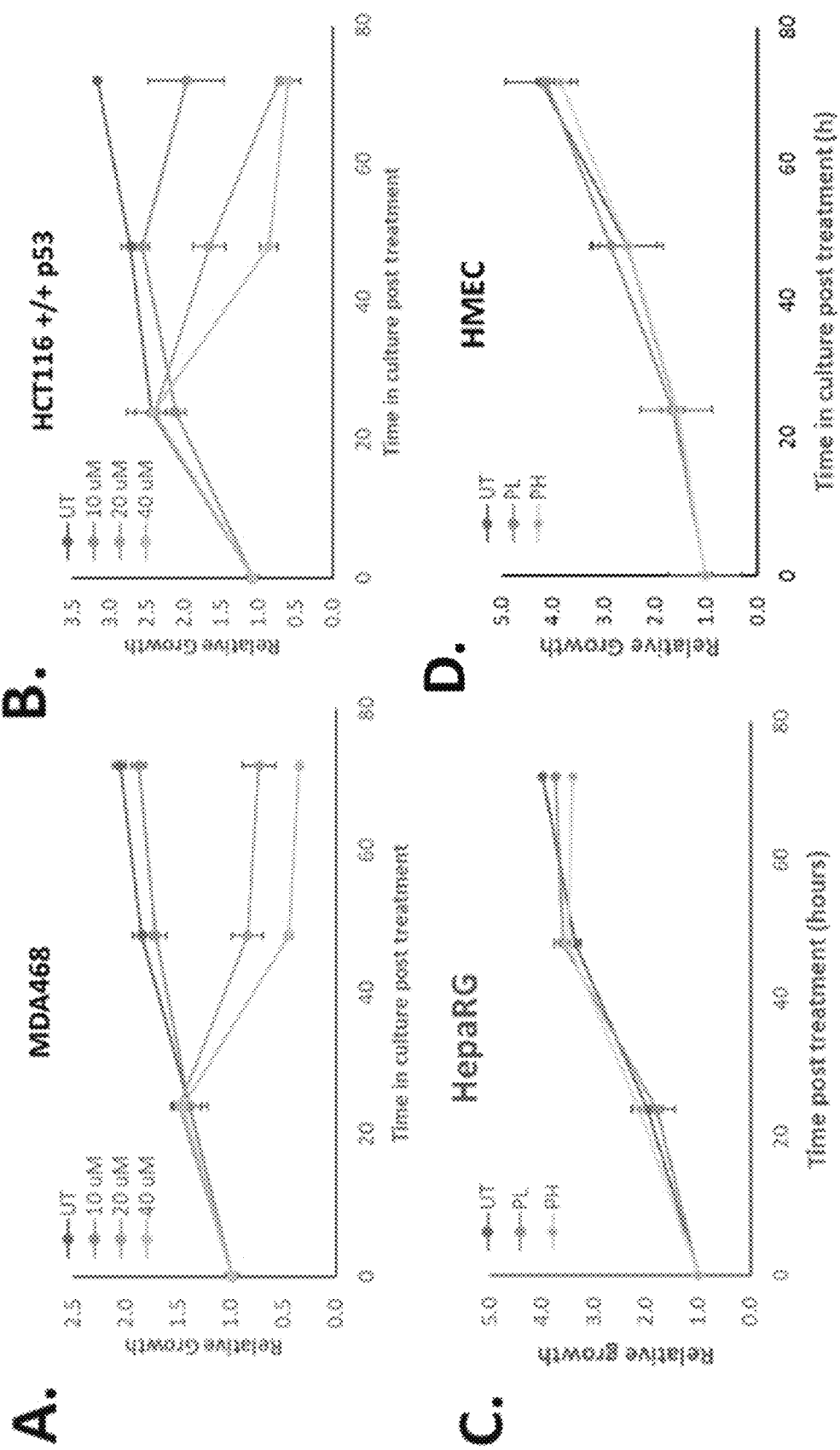
FIG. 20A-D

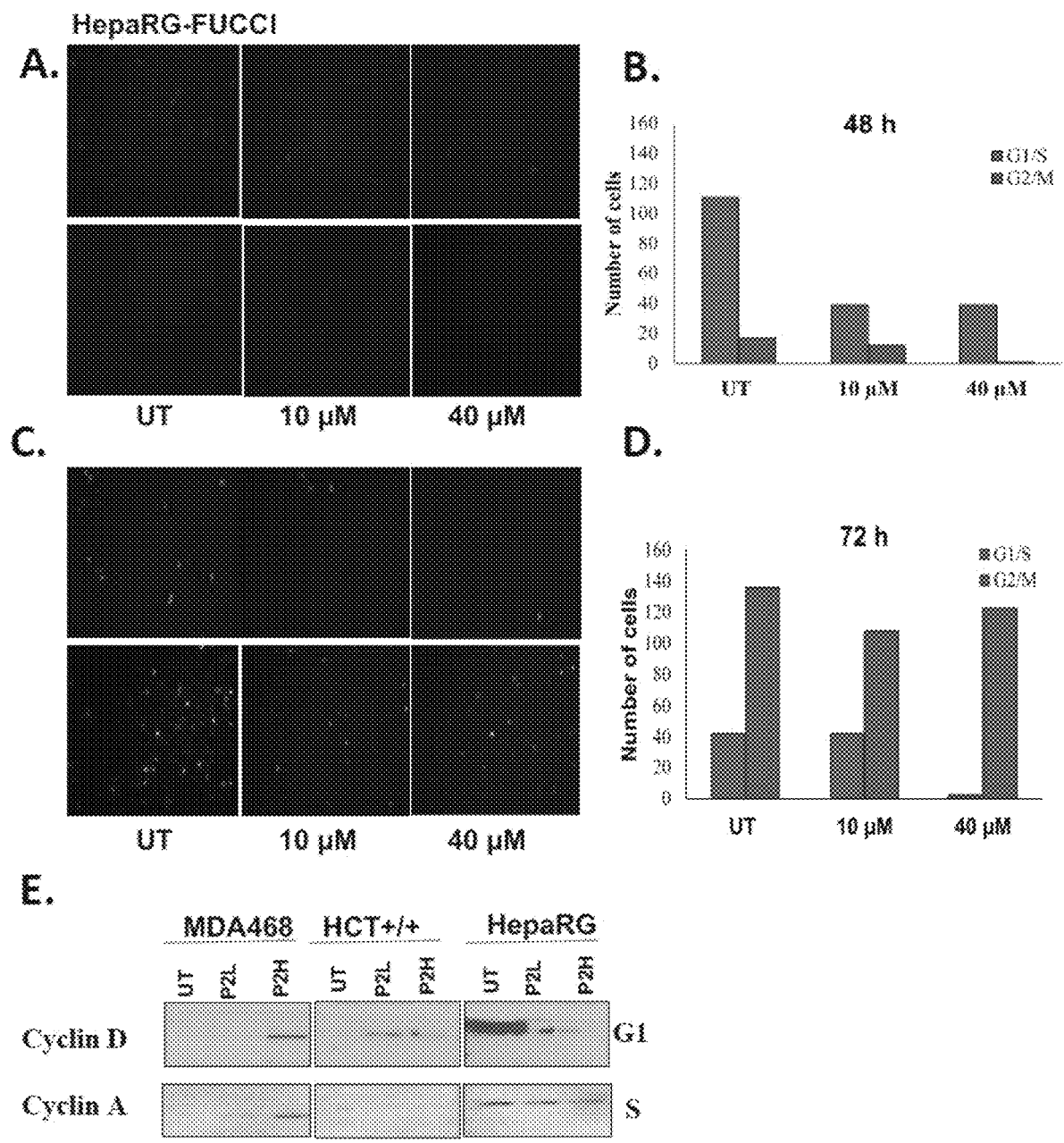
FIG. 21A-E

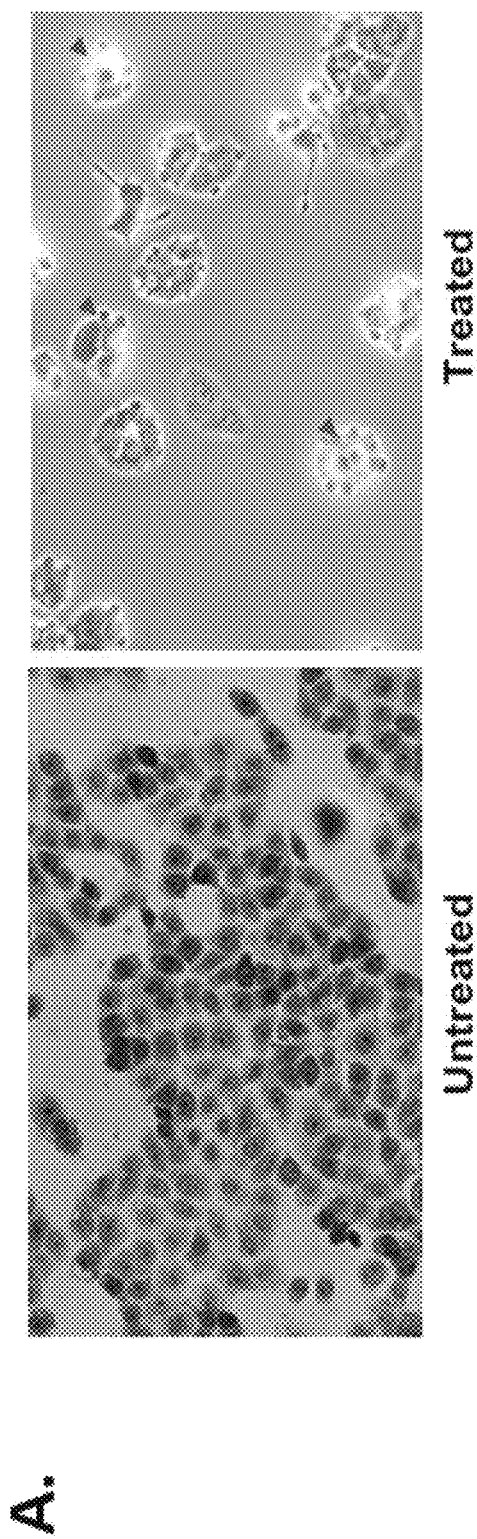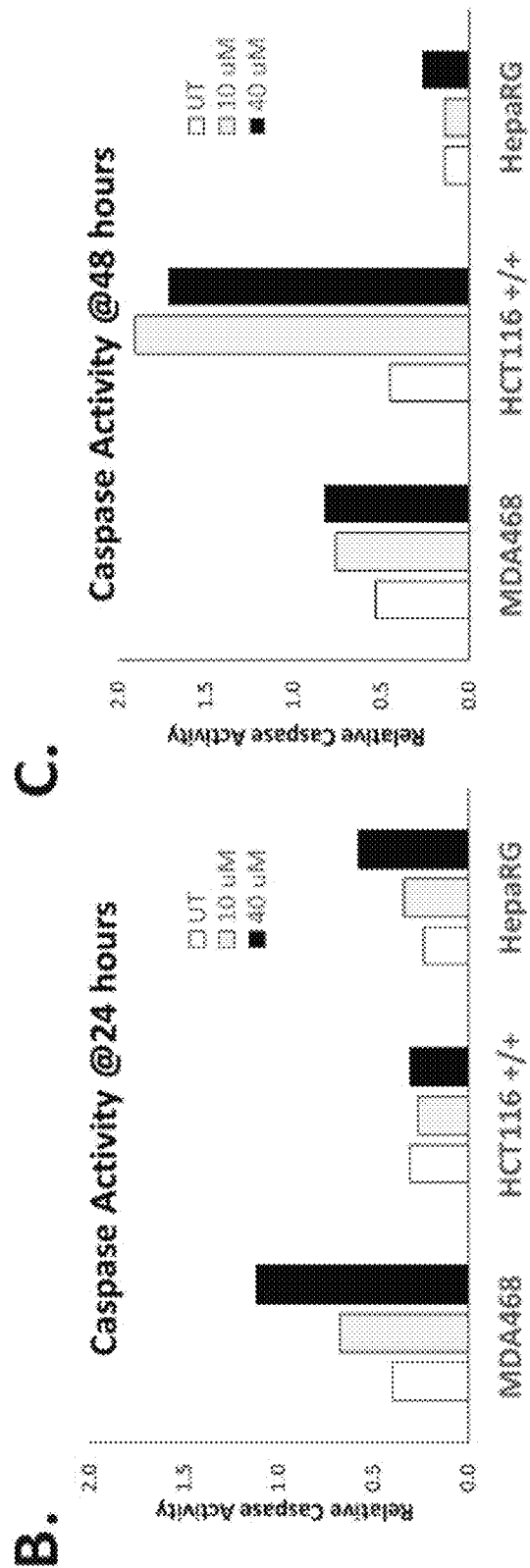
FIG. 22A-C

A.
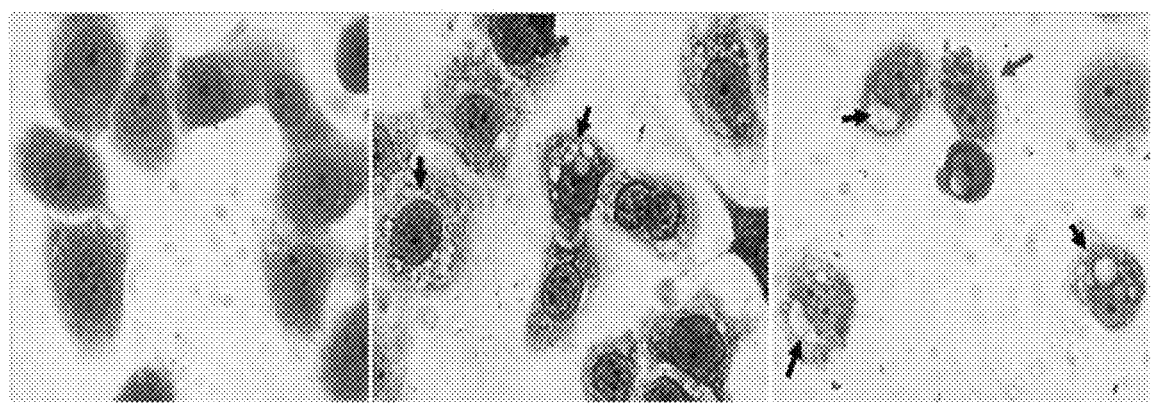
B.
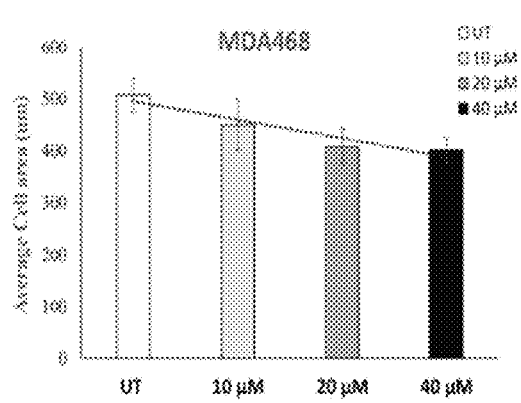
C.
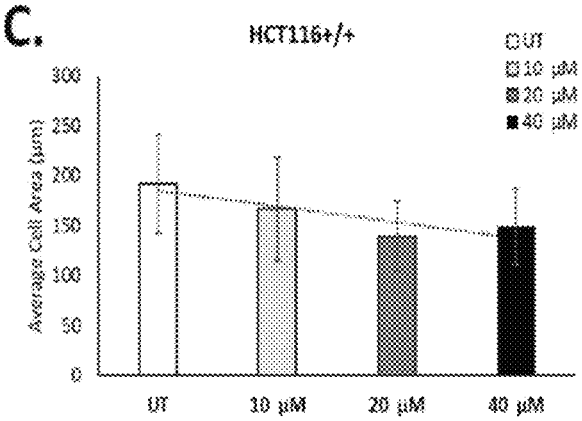
D.
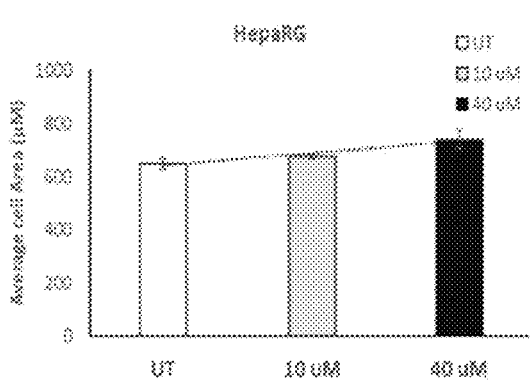
E.
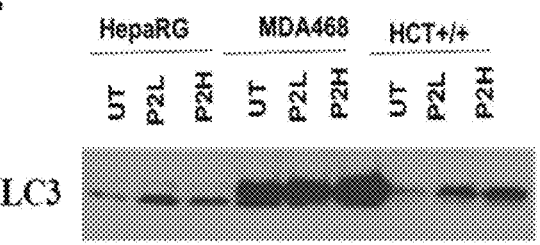
FIG. 23A-E

PEPTOID-BASED INHIBITORS OF THE PROTEIN ARGININE METHYLTRANSFERASE (PRMT) FAMILY

CROSS REFERENCE TO RELATED APPLICATIONS

This application is a divisional of and claims priority to U.S. Nonprovisional application Ser. No. 17/527,475, entitled "Peptoid-Based Inhibitors of the Protein Arginine Methyltransferase (PRMT) Family", filed Nov. 16, 2021, which is a nonprovisional of and claims priority to U.S. Provisional Application No. 63/114,813 entitled "Peptoid-Based Inhibitors of the Protein Arginine Methyltransferase (PRMT) Family", filed Nov. 17, 2020, the contents of which are hereby incorporated by reference into this disclosure.

FIELD OF INVENTION

This invention relates to compounds and methods of treatment for PRMT associated diseases. Specifically, the invention provides novel peptide mimetics that target the PRMT family.

BACKGROUND OF THE INVENTION

The transcription of cancer-related genes can be altered as a result of the post-translational modifications catalyzed by histone-modifying enzymes on residues found within the N-terminal tails of histones. These modifications, which include lysine (acetylation, methylation), serine (phosphorylation), and arginine (methylation) have been shown to affect physiological homeostasis [1,2]. The methylation of arginine residues is catalyzed by protein arginine methyltransferases (PRMTs), a family of 11 isozymes that are sub-divided into three types based on their methylation products.

Type I PRMTs catalyze the ω-asymmetric dimethylation of arginine and include PRMT1, 2, 3, 4, 6, 8, 10, and 11. Type II PRMTs, which include PRMT5 and PRMT9, catalyze the ω-symmetric dimethylation of arginine. The lone Type III PRMT (PRMT7) produces only monomethylated arginine products [3-6].

All of the PRMT family members modify arginine residues within the N-terminal tails of histone proteins (FIG. 1). Specific arginine modifications can be attributed to the recruitment of certain isozymes by transcription factors that are bound to the histone, as well as the substrate specificity due to particular amino acid sequences and histone marks surrounding the site of modification [2]. Some notable differences in the substrate specificity among the isozymes have been recently determined using high-throughput screening methodologies, mass spectrometry techniques, and detailed kinetic analyses [7-18]. Although these studies have identified novel isozyme-specific PRMT substrates, the precise factors that lead to the recruitment of and catalysis by specific PRMT isozymes remains unclear [19]. Elucidation of these factors would allow for targeting specific members of the PRMT family and would be beneficial due to some of their antagonistic relationships. For example, the transcriptional activation of ERα and p53 leads to the onset and progression of cancer-related genes. Transcription of these genes is activated as a result of the asymmetric dimethylation of Histone H4 at Arg3 by PRMT1, yet these same genes are repressed as a result of symmetric dimethylation of the same Arg by PRMT5 [20-25]. Thus, the development of selective inhibitors that target specific isozymes could provide a mechanism to restrict the catalytic activity of one isozyme, while permitting catalytic activity of the other PRMT family members.

A recent study identified a novel PRMT1 peptide-based substrate that is not modified by PRMT5. This PRMT1-specific peptide substrate was converted into a chemical probe that selectively labels PRMT1 over PRMT5 [19]. To date, most chemical probes or inhibitors target PRMT enzymes with a combination of SAM-analogues, small molecules, and peptide-based inhibitors [26-30]. Although SAM-analogues and small molecules can be specific, most lead to a number of off-target effects [31,32].

Peptide-based inhibitors can provide selectivity among enzymes, but are susceptible to proteolysis thus limiting their in vivo utility rendering them unsuitable as clinical therapeutics. To circumvent the problems associated with proteolysis, a class of peptide mimetics known as peptoids are sometimes employed.

First reported in the 1990s, peptoids, contain ordered sequence composition, diverse side chains, and can be constructed rapidly by sub-monomer synthesis [33]. The peptoid-scaffold is less susceptible to degradation because the side chain is attached to the nitrogen in the amide backbone instead of the α-carbon, thus rendering them more robust against proteases [34]. Because the overall sidechain structure is largely conserved, the mode of binding and mechanism of action may also be well preserved. Peptoids composed of amino acid mimetics and non-amino acid monomers have been used as ligands to capture proteins [35,36]. Furthermore, the use of peptoid-based inhibitors has been reported for enzymes and as antimicrobial compounds [37,38]. However, there are very few reports of measuring the kinetic parameters of peptoids that were modeled on well-characterized peptide substrates [39,40].

Given the advantages of peptoid stability, the inventors sought to compare the kinetic parameters of peptoid substrates against known peptide substrates of PRMT family members. Previous kinetic studies have identified that histone-based peptides of the N-terminal tails are good models of the full-length histones, so the inventors focused on the peptoids that mimic the N-terminal tail of Histone H4. The inventors found that not only are the peptoid versions of the Histone H4 N-terminal tail poor substrates for PRMT1, these peptoids inhibit the enzymatic activity of this isozyme. Furthermore, this exhibited inhibition is moderately selective for PRMT1 over PRMT5 and suggest that selectivity among family members is possible.

SUMMARY OF INVENTION

Methylation of arginine residues occurs on a number of protein substrates, most notably the N-terminal tails of histones, and is catalyzed by a family of enzymes called the protein arginine methyltransferases (PRMTs). This modification can lead to transcriptional activation or repression of cancer-related genes. To date, a number of inhibitors, based on natural peptide substrates, have been developed for the PRMT family of enzymes. However, because peptides are easily degraded in vivo, the utility of these inhibitors as potential therapeutics is limited.

The use of peptoids, which are peptide mimetics where the amino acid side chain is attached to the nitrogen in the amide backbone instead of the α-carbon, may circumvent the problems associated with peptide degradation. Given the structural similarities, peptoid scaffolds may provide enhanced stability, while preserving the mechanism of action. The inventors have identified that peptoids based on natural peptide substrates are not catalyzed to the product by PRMT1, but instead are inhibitors of this enzyme. Reducing the length of the peptoid reduces inhibition and suggest the residues distal from the site of modification are important for binding. Furthermore, a positive charge on the N-terminus helps promote binding and improves inhibition. Selectivity among family members is likely possible based on inhibition being moderately selective for PRMT1 over PRMT5 and provides a scaffold used to develop pharmaceuticals against this class of enzymes.

In an embodiment, a compound for inhibiting protein arginine methyltransferase (PRMT) is presented comprising a peptide mimetic such as a peptoid-based inhibitor of PRMT that mimics the N-terminal tail of histone H4, particularly Histone H4-16, Histone-H4-13, or Histone H4-8 peptide. In some embodiments, the peptoid-based inhibitor is unacetylated and the PRMT inhibited is PRMT1 or PRMT5.

In some embodiments, the structure of the peptide mimetic comprises:

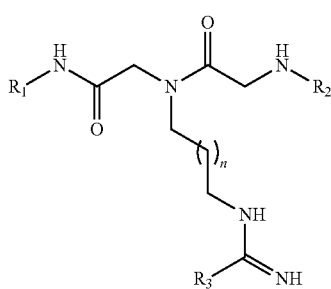

(I)

wherein $R_1$ is at least one amine monomer;
wherein $R_2$ is at least one amine monomer;
wherein $R_3$ is $NH_2$ or $CH_2$—X;
wherein X is a halogen; and wherein n is an integer between 1 and 4.

In some embodiments, $R_3$ is $CH_2$—X and X is selected from the group consisting of chlorine (Cl), iodine (I), flourine (F), bromine (Br), astatine (At), and tennessine (Ts).

In another embodiment, the compounds described above may be combined with a pharmaceutically acceptable carrier to form a composition for inhibiting protein arginine methyltransferase (PRMT).

In a further embodiment, a method of inducing apoptosis in at least one cancer cell is presented comprising administering a therapeutically effective amount of a peptide mimetic to the at least one cancer cell wherein the peptide mimetic is a peptoid-based inhibitor of protein arginine methyltransferase (PRMT).

The structure of the peptoid-based inhibitor used to induce apoptosis may be that of Formula (II) below:

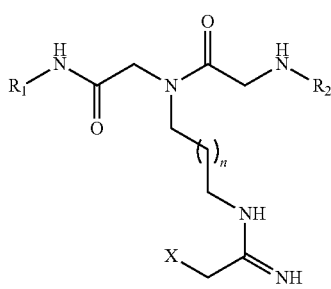

(II)

wherein $R_1$ is at least one amine monomer;
wherein $R_2$ is at least one amine monomer;
wherein X is a halogen; and wherein n is an integer between 1 and 4.

X may be selected from the group consisting of chlorine (Cl), iodine (I), flourine (F), bromine (Br), astatine (At), and tennessine (Ts). In some embodiments, the halogen is chlorine (Cl). In some embodiments, the peptoid-based inhibitor is unacetylated.

In some embodiments, the peptoid-based inhibitor of PRMT that induces apoptosis may mimic the N-terminal tail of histone H4, particularly Histone H4-16, Histone-H4-13, or Histone H4-8 peptide. In some embodiments, the peptoid-based inhibitor is unacetylated and the PRMT inhibited is PRMT1 or PRMT5.

In another embodiment, a method of inhibiting protein arginine methyltransferase (PRMT) is presented comprising administering a therapeutically effective amount of the compound or composition to a patient in need thereof. In some cases, this inhibition of PRMT can be used to treat a PRMT-associated disorder such as cancer.

In some embodiments, the compound used to inhibit PRMT has the structure of Formula (I) below:

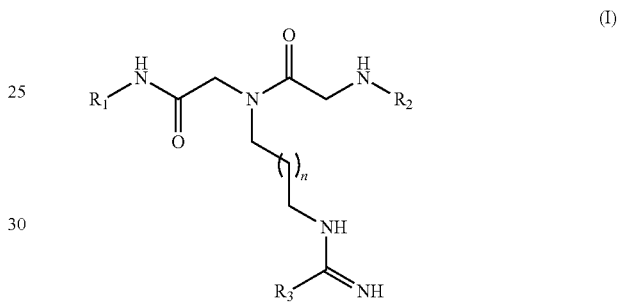

(I)

wherein $R_1$ is at least one amine monomer;
wherein $R_2$ is at least one amine monomer;
wherein $R_3$ is $NH_2$ or $CH_2$—X;
wherein X is a halogen; and wherein n is an integer between 1 and 4.

In some embodiments, $R_3$ is $CH_2$—X and X is selected from the group consisting of chlorine (Cl), iodine (I), flourine (F), bromine (Br), astatine (At), and tennessine (Ts).

The peptoid-based inhibitor of PRMT may mimic the N-terminal tail of histone H4, particularly Histone H4-16, Histone-H4-13, or Histone H4-8 peptide. In some embodiments, the peptoid-based inhibitor is unacetylated and the PRMT inhibited is PRMT1 or PRMT5.

BRIEF DESCRIPTION OF THE DRAWINGS

For a fuller understanding of the invention, reference should be made to the following detailed description, taken in connection with the accompanying drawings, in which.

Figure 1:
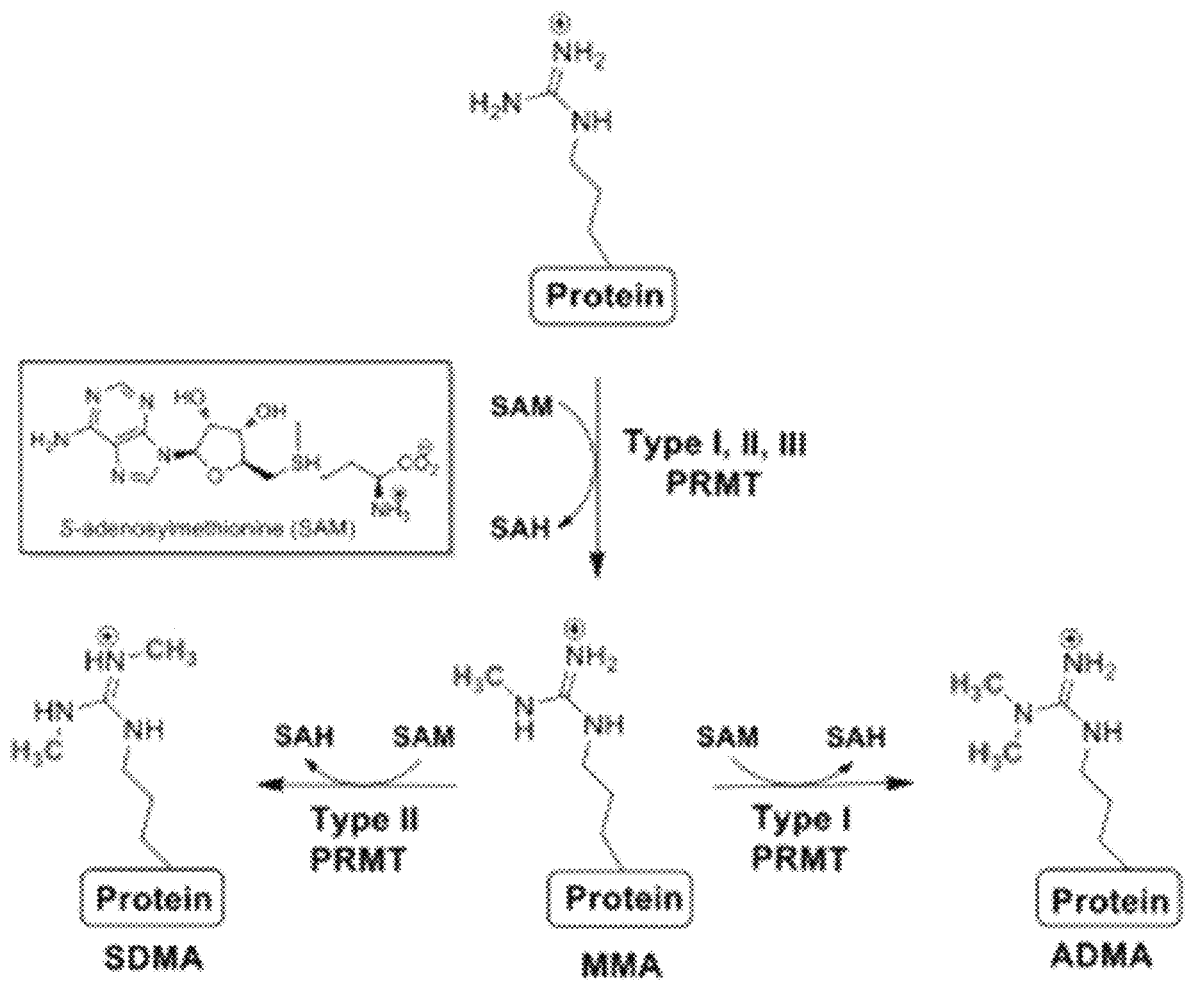
FIG. 1 is an image depicting the reaction catalyzed by protein arginine methyltransferase family of enzymes is described in a three-step process. PRMTs transfer a methyl group from S-adenosylmethionine (SAM) to the side chain of arginine to produce monomethylarginine (MMA). Type I PRMTs result in the production of asymmetric dimethylarginine (ADMA) and Type II PRMTs result in the production of symmetric dimethylarginine (SDMA). A Type III PRMT only catalyzes the formation of MMA.

Sodium hydroxide (600 mg, 15 mmol) was added to a solution of N-(2-trityloxyethyl)-2,2,2-trifluoroacetamide (2) (303 mg, 1.0 mmol) dissolved in MeOH (12 mL). The mixture was refluxed until for 2 h and then concentrated under reduced pressure. The residue was partitioned between DCM and water (12.5 mL each) and the aqueous layer was extracted with twice more with DCM. The organics were combined, washed with brine (10 mL), dried over sodium sulfate, and concentrated under reduced pressure to afford the product (3) in quantitative yield. $^1$H NMR ($CDCl_3$): 7.51 (m, 6H), 7.35 (m, 6H), 7.21 (m, 3H), 3.69 (t, J=5.5, 2H), 2.38 (m, 2H), 1.89 (t, J=8.0).

Figure 4:
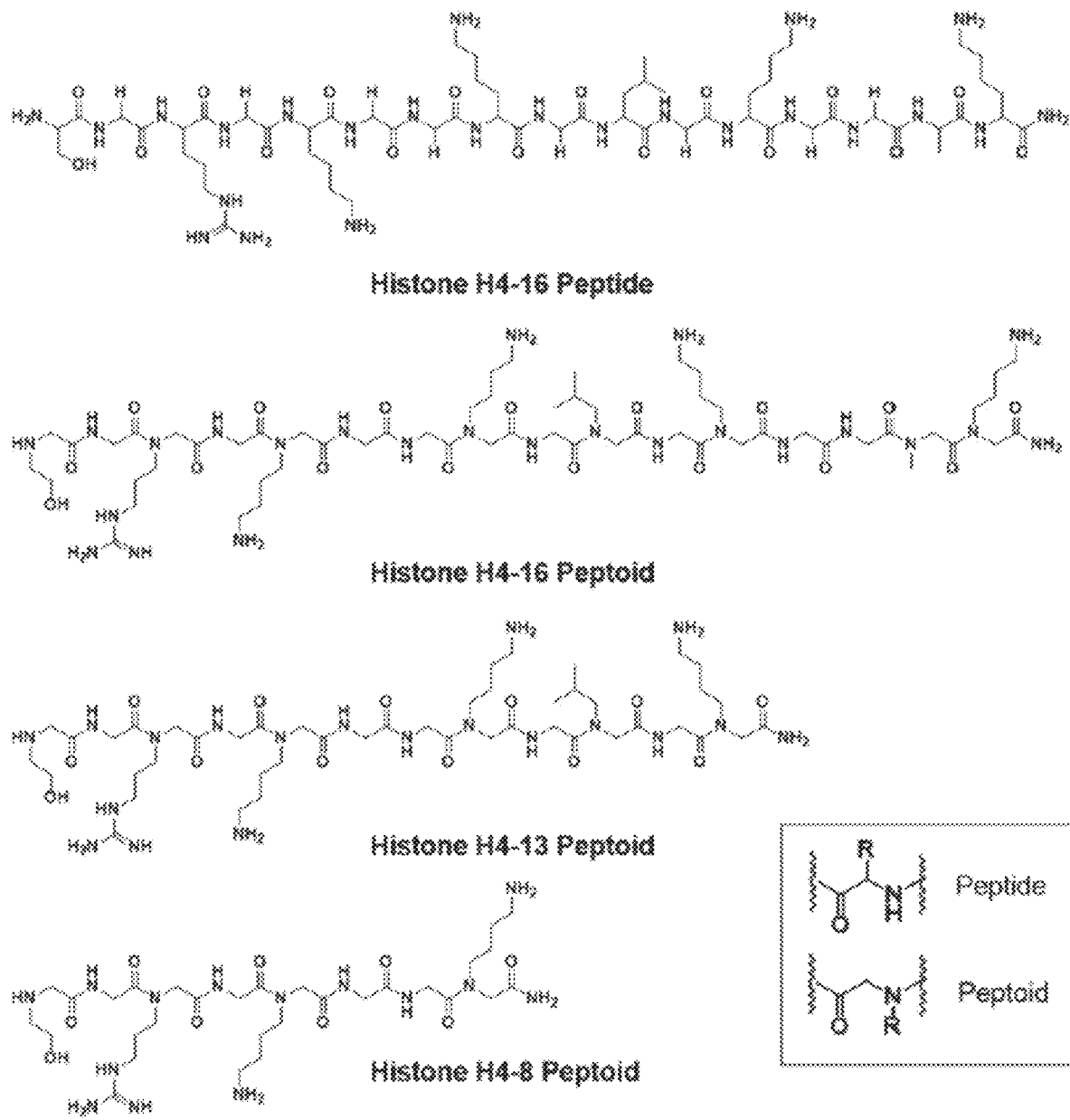
Figure 10:
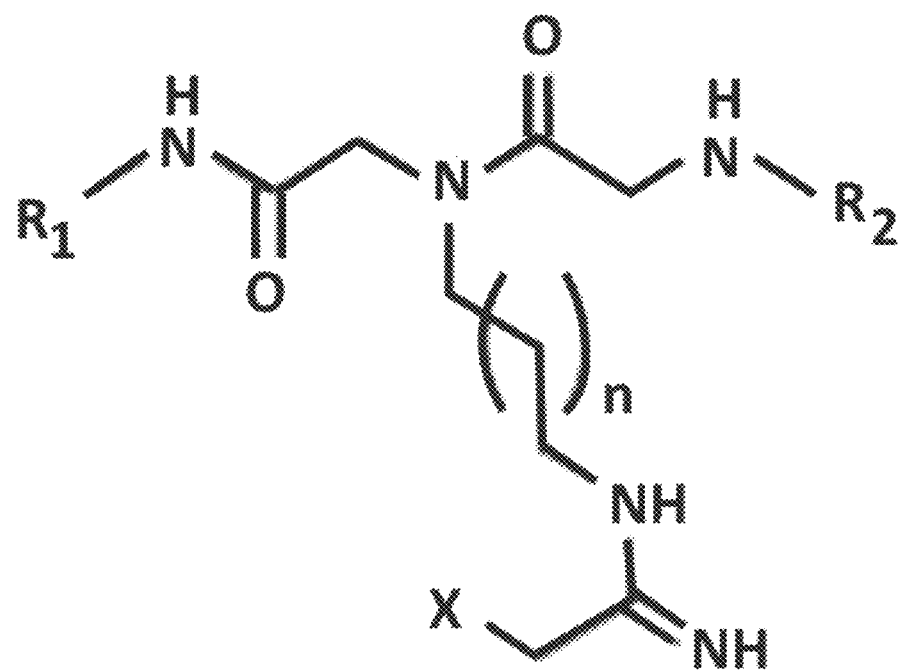

FIG. 4 is an image depicting the structure of the histone H4-16 peptide versus the H4-16, H4-13 and H4-8 peptoid. The inset shows the differences in the location of the side chain between a peptide and a peptoid. In some embodiments, the R group on the peptoid may be an acetamidine group including but not limited to, a haloacetamidine group as shown in FIG. 10.

Figure 5:
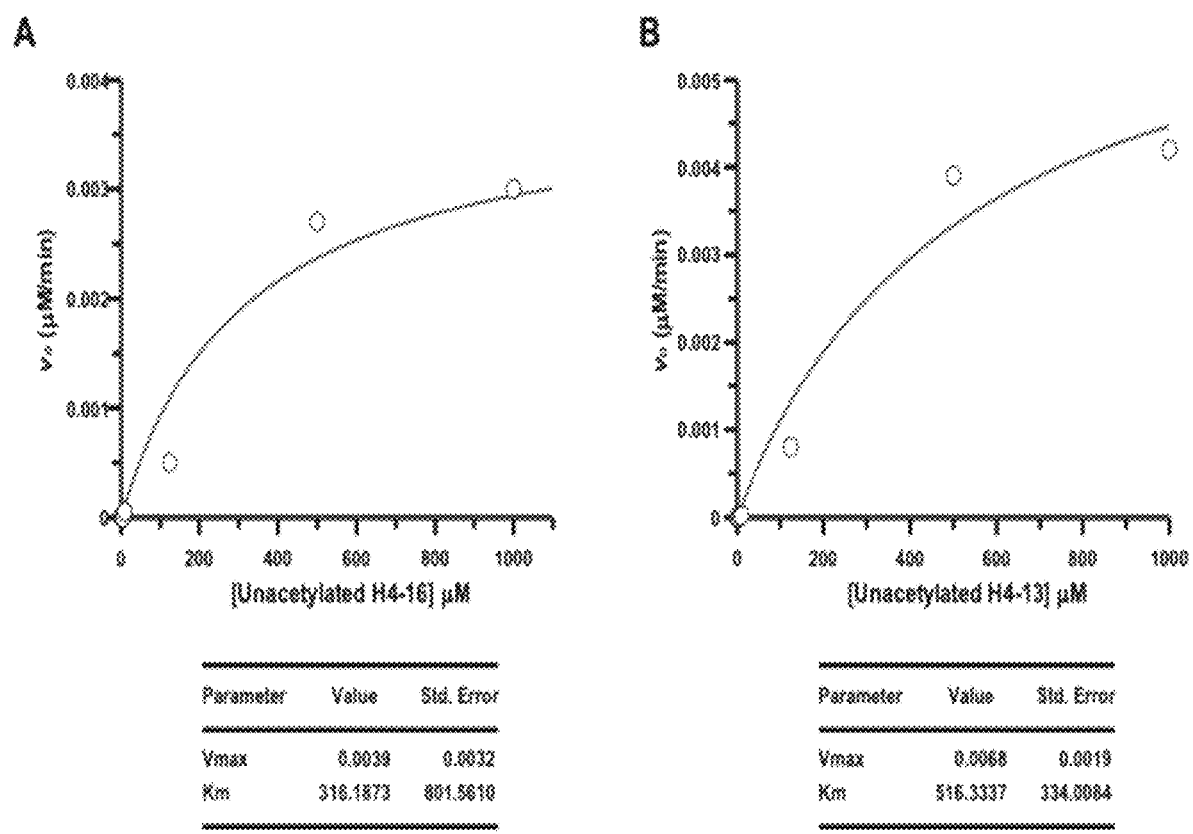

FIG. 5A-B are graphs depicting determination of the kinetic parameters of peptoids. Michaelis-Menten plots for (A) unacetylated H4-16 and (B) unacetylated H4-13 peptoids with PRMT1.

FIG. 6 is a graph depicting $IC_{50}$ plot for acetylated H4-16 with PRMT1.

FIG. 7A-B are graphs depicting $IC_{50}$ plot for (A) acetylated H4-13 and (B) unacetylated H4-13 with PRMT1.

FIG. 8A-B are graphs depicting $IC_{50}$ plot for (A) acetylated H4-8 and (B) unacetylated H4-8 with PRMT1.

FIG. 9A-B are graphs depicting the $IC_{50}$ plots of (A) PRMT1 and (B) PRMT5 with the unacetylated H4-16 peptoid.

FIG. 10 is an image of an exemplary compound of the instant invention including a haloacetamidine warhead. Peptoids of varying lengths and monomer units may incorporate a haloacetamidine warhead as shown in the image. The carbon chain length (n) can vary within the compound between 1 to 4. X can be any halogen element including chlorine (Cl), iodine (I), flourine (F), bromine (Br), astatine (At), or tennessine (Ts).

FIG. 11 is a series of images depicting an acetylated H4-16 warhead peptide and an unacetylated H4-16 warhead peptide.

Figure 12:
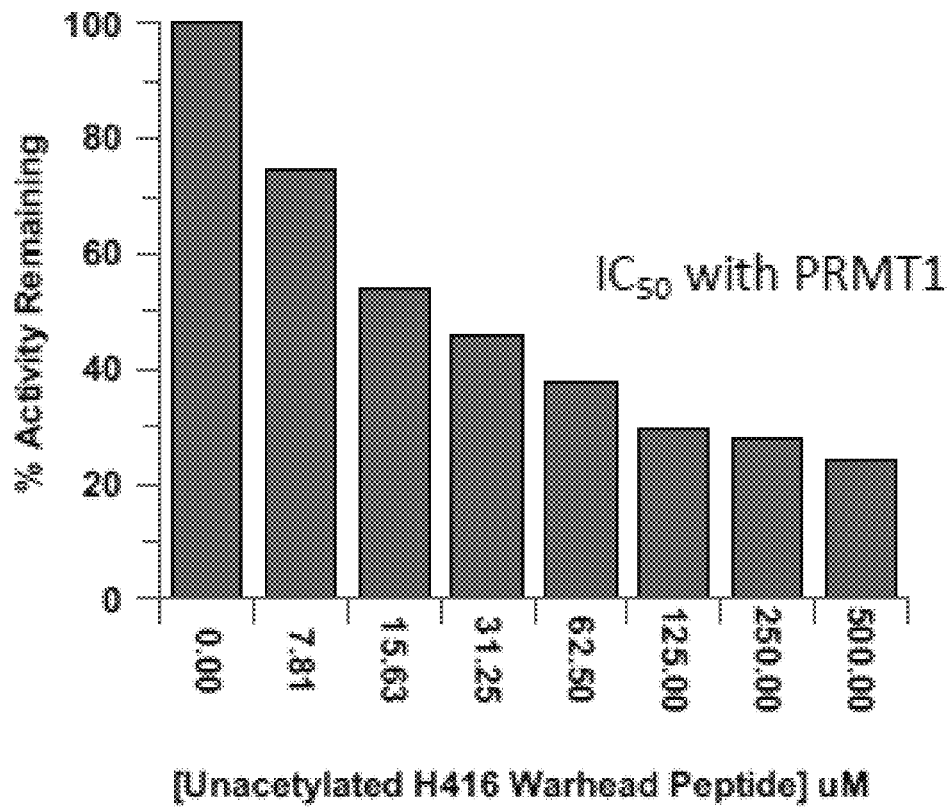

FIG. 12 is a graph depicting the $IC_{50}$ plot of PRMT1 with the unacetylated H4-16 warhead peptide.

Figure 13:
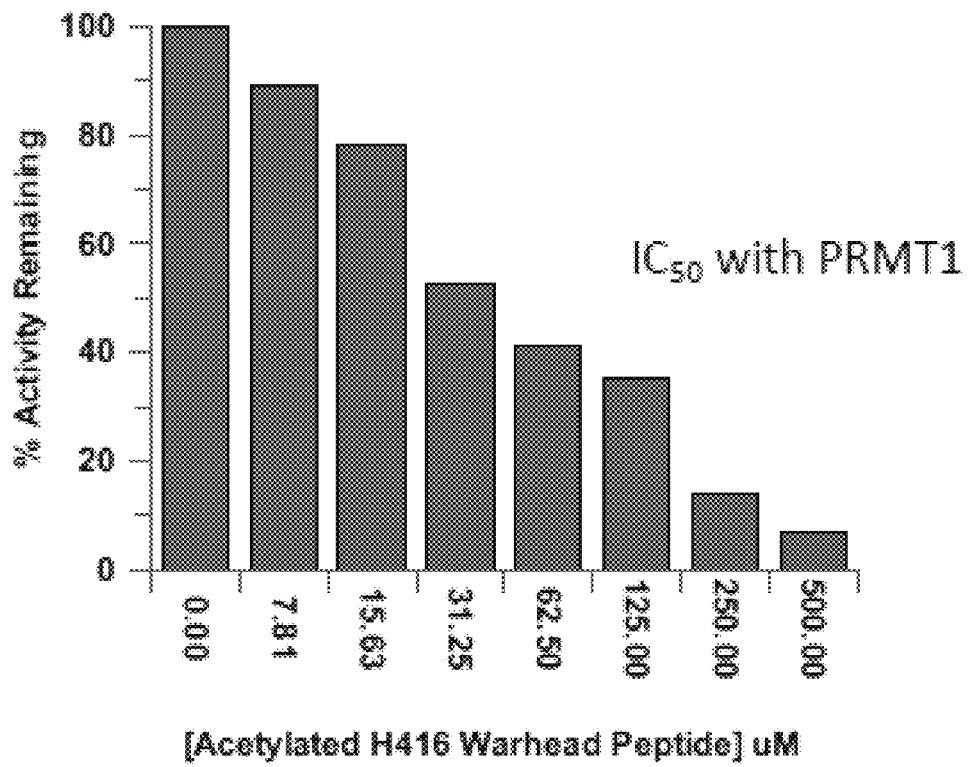

FIG. 13 is a graph depicting the $IC_{50}$ plot of PRMT 1 with the acetylated H4-16 warhead peptide.

Figure 14:
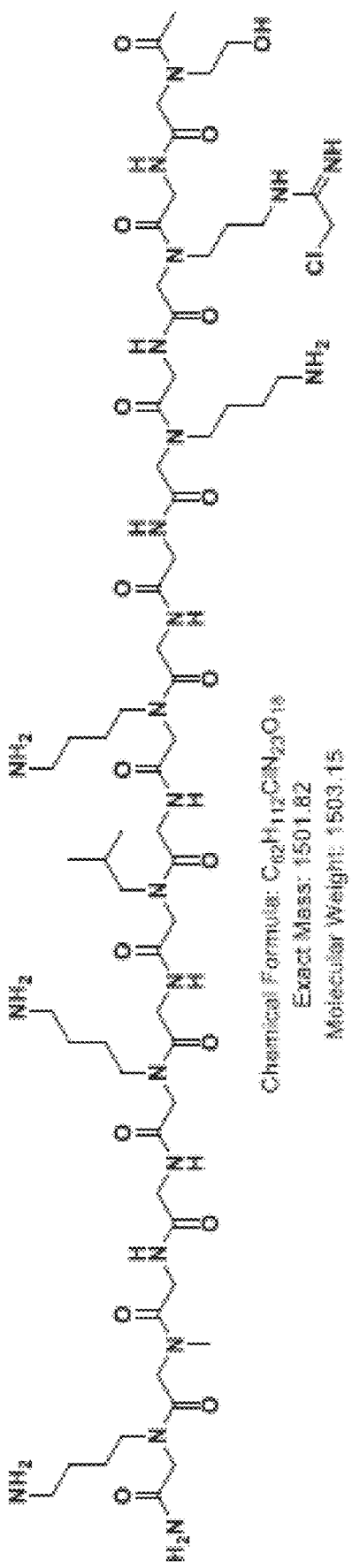

FIG. 14 is an image of the H4-16 warhead chloracetamidine peptoid inhibitor.

FIG. 15 is a series of images depicting an acetylated H4-16 warhead chloracetamidine peptoid inhibitor and an unacetylated H4-16 warhead chloracetamidine peptoid inhibitor.

Figure 16:
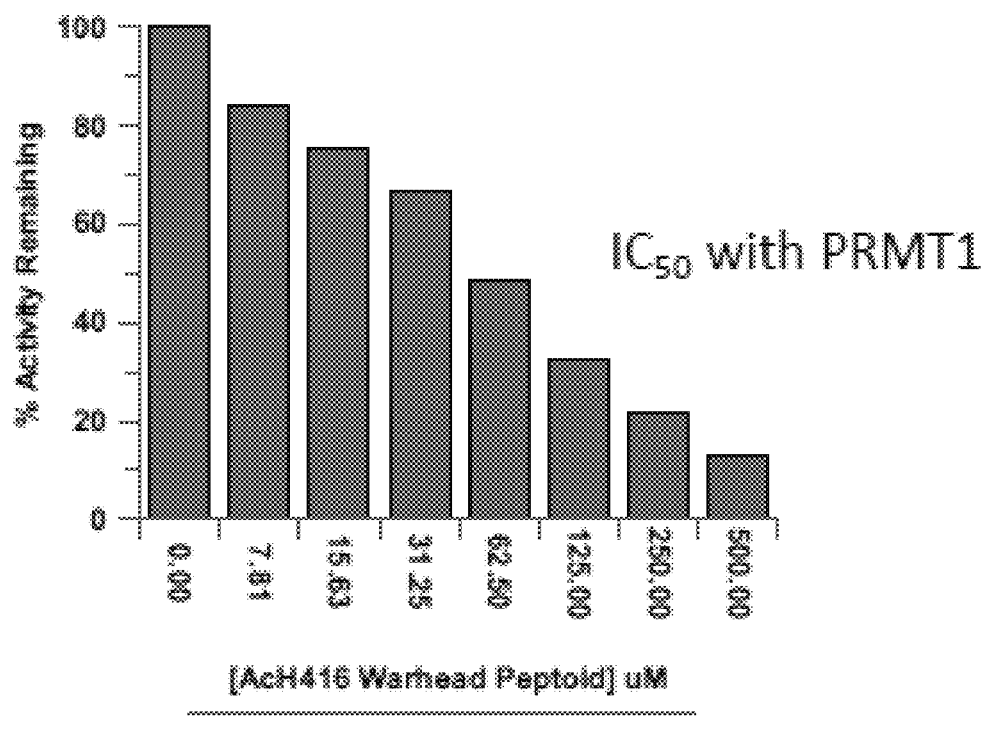

FIG. 16 is a graph depicting the $IC_{50}$ plot of PRMT 1 with the acetylated H4-16 warhead peptoid.

Figure 17:
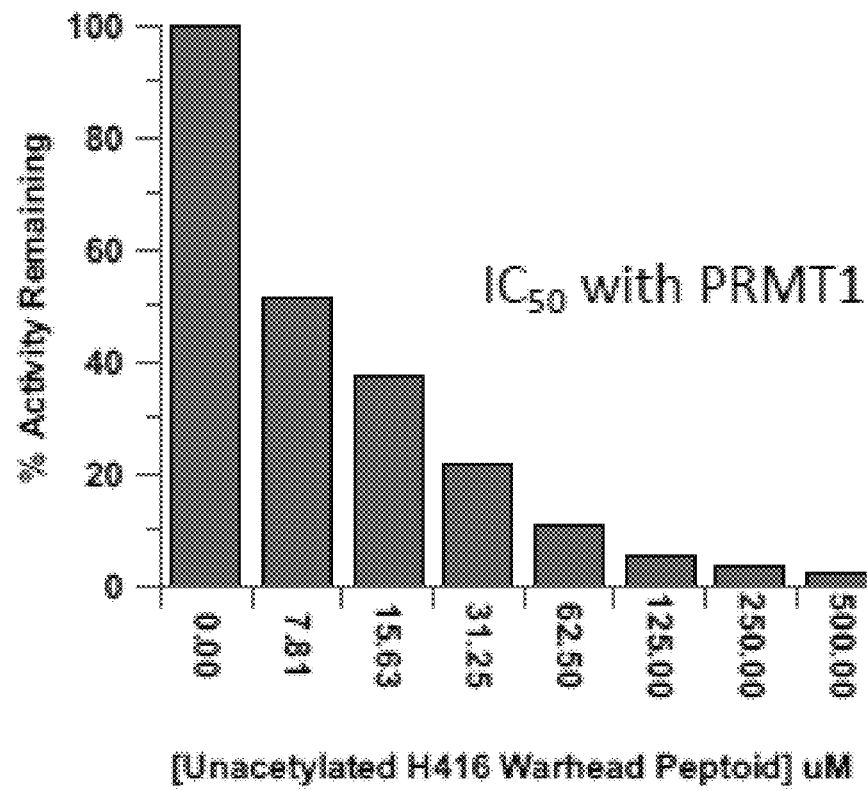

FIG. 17 is a graph depicting the $IC_{50}$ plot of PRMT1 with the unacetylated H4-16 warhead peptoid.

Figure 18:
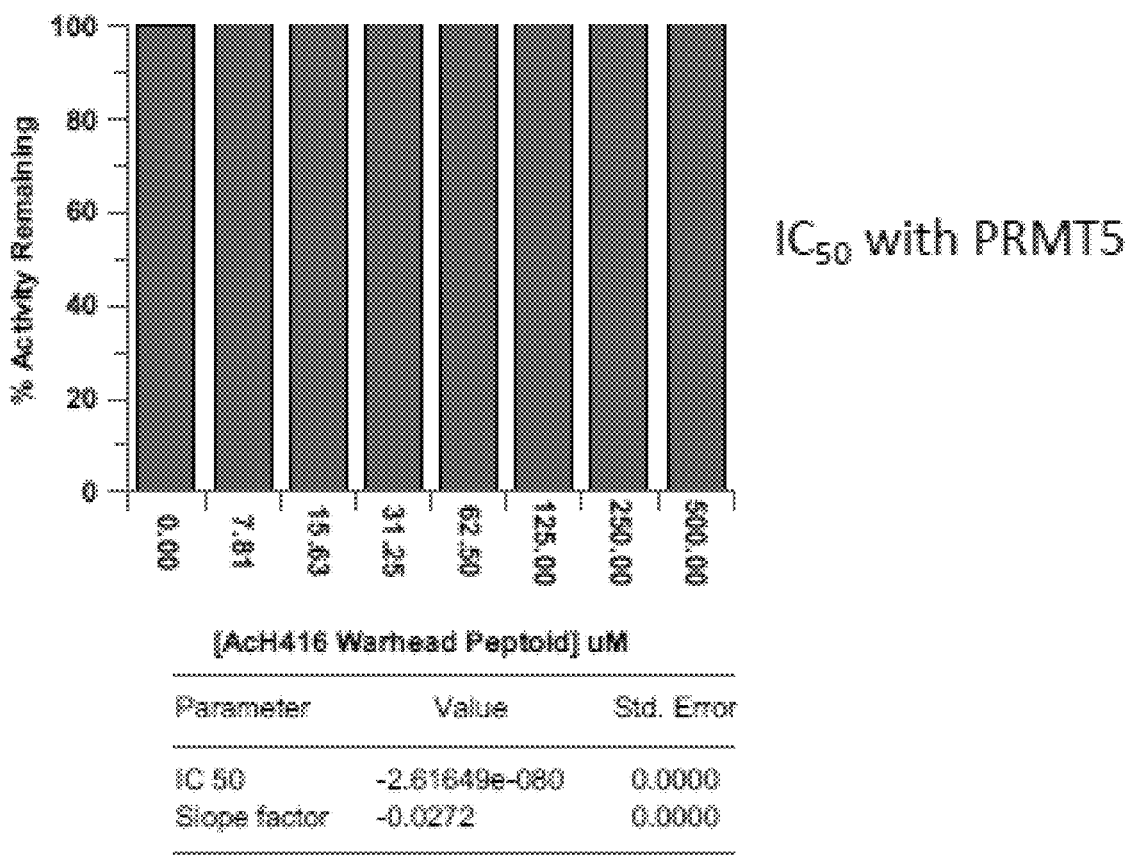

FIG. 18 is a graph depicting the $IC_{50}$ plot of PRMT5 with the acetylated H4-16 warhead peptoid.

FIG. 19A-B are a series of images depicting the PRMT inhibitor (unacetylated H4-16 warhead chloracetamidine peptoid) reduces cell growth and viability specifically in cancer and not in normal cells. (A) MDA468 breast carcinoma cells, HCT-116 colon carcinoma cells, and HepaRG immortalized, terminally differentiated liver cells were grown in the presence of various concentrations of the P2 compound (0-40 PM) for 48 hours and cell viability was assessed using crystal violet assay; (B) graph depicting the compound has a significant anti-proliferative affect in a dose-response manner on both cancer cells while no prominent change was seen in the viability of the non-tumorigenic HepaRG cells (p<0.01).

FIG. 20A-D are a series of graphs depicting the PRMT inhibitor (unacetylated H4-16 warhead chloracetamidine peptoid) reduces cancer cell viability in a dose and time dependent manner in (A) MDA468 breast carcinoma cells and (B) HCT-116 colon carcinoma cells. No detectable effect in growth was exhibited in non-tumorigenic (C) HepaRG liver cells or (D) human mammary epithelial cells (HMEC). As such, the compound specifically targets cancer cells and reduces their viability and growth potential without significant toxicity to normal and non-tumorigenic cells.

FIG. 21A-E are a series of images depicting that extended treatment with the PRMT inhibitor (unacetylated H4-16 warhead chloracetamidine peptoid) may induce growth arrest. HepaRG-FUCCI cells were used to follow the cell cycle in real time in the presence or absence of P2 in the media. (A and B) Significant reduction of cells entering cell cycle was seen after 48 hours of P2 treatment indicating that new cell cycle was inhibited by the compound; (C and D) Similar numbers of cells were seen in G2/M phase however, both at 48 and 72 hours of P2 treatment; (E) Western blot analysis confirmed reduced number of cells entering G1 and S phase with inhibition of Cyclin D and A respectively in HepaRG cells. Both MDA468 and HCT116 cells however, showed little change in Cyclin D or Cyclin A expression possibly indicating minimal effect on cell cycle of cancer cells.

FIG. 22A-C are a series of images depicting the PRMT inhibitor (unacetylated H4-16 warhead chloracetamidine peptoid) induces apoptosis in cancer cells. (A) Cell morphology was examined in untreated and treated cells to determine apoptosis. Untreated cells remained healthy and normal in appearance throughout experimental time frame while several cells in the treated samples showed membrane blebbing, rounding and presence of small vacuoles which could all indicate apoptosis; (B) significant caspase-3 activity shown in a dose response manner in MDA468 cells after 24 hours; and (C) significant caspase-3 activity shown in a dose response manner in HCT116 cells after 48 hours. Only minimal activation of caspase-3 was exhibited in HepaRG cells and only at the highest dose.

FIG. 23A-E are a series of images depicting markers of autophagy exhibited in response to treatment with the PRMT inhibitor (unacetylated H4-16 warhead chloracetamidine peptoid). (A) (left) untreated MDA468 cells, (center) MDA468 cells treated with 20 µM PRMT inhibitor, (right) MDA468 cells treated with 40 µM PRMT inhibitor. As shown in the images, a large percentage of treated cells exhibit vacuoles which is indicative of autophagy; (B) significant decrease in size shown in MDA468 cells after treatment with the PRMT inhibitor; (C) significant decrease in size shown in HCT116 cells after treatment with the PRMT inhibitor; (D) no significant change in size shown in HepaRG cells after treatment with the PRMT inhibitor; (E) Western blot confirms activation of autophagy in all three cell lines in response to treatment with the PRMT inhibitor.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.
Abbreviations
  COPD—chronic obstructive pulmonary disease
  H4—histone 4
  PRMT—protein arginine methyltransferase
  SAH—S-adenosylhomocysteine
  SAM—s-adenosylmethionine
Definitions As used herein, the singular forms "a," "an" and "the" include plural referents unless the context clearly dictates otherwise.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, "about" means approximately or nearly and in the context of a numerical value or range set forth means±10% of the numerical.

As used herein "patient" is used to describe an animal, preferably a human, to whom treatment is administered, including prophylactic treatment with the compositions of the present invention. "Patient" is used interchangeably with "subject" herein.

As used herein "animal" means a multicellular, eukaryotic organism classified in the kingdom Animalia or Metazoa. The term includes, but is not limited to, mammals. Non-limiting examples include rodents, mammals, aquatic mammals, domestic animals such as dogs and cats, farm animals such as sheep, pigs, cows and horses, and humans. Wherein the terms "animal" or the plural "animals" are used, it is contemplated that it also applies to any animals.

The term "PRMT-associated disease" as used herein refers to diseases or conditions characterized by involvement of PRMTs in the disease state. Examples of PRMT-associated diseases include, but are not limited to, cancers; cardiovascular diseases; pulmonary diseases including, but not limited to, pulmonary fibrosis, pulmonary hypertension, chronic obstructive pulmonary disease (COPD), asthma, and lung cancer; viral infections; neurodegenerative disorders; muscular disorders including neuromuscular disorders; metabolic disorders; and inflammatory conditions.

The term "cancer" as used herein refers to any physiological condition in mammals characterized by unregulated cell growth. Examples of cancers associated with PRMT include, but are not limited to, hematologic and solid tumor types such as lung cancers, including both small cell lung cancers and non-small cell lung cancers; breast cancers; colon cancer; bladder cancer; leukemia; hepatocellular carcinoma; lymphomas; prostate cancer; ovarian cancer; glioblastoma; melanoma and other skin cancers; gastric cancer; and germ cell cancers, among others. The term "cancer" is used synonymously with "neoplasia" herein.

The term "neurodegenerative disease" refers to any abnormal physical or mental behavior or experience where the death or dysfunction of neuronal cells is involved in the etiology of the disorder. Examples of neurodegenerative diseases include, but are not limited to, Alzheimer's disease, Parkinson's disease, Huntington's disease, dementia, amyotrophic lateral sclerosis (ALS), and multiple sclerosis.

The term "PRMT inhibitor" as used herein refers to a compound that is capable of inhibiting at least one PRMT. In some embodiments the PRMT inhibitor is a peptide mimetic such as a peptoid-based inhibitor. In some embodiments, the peptoid mimics the N-terminal tail of one or more histones. In some embodiments, the peptoid mimics the N-terminal tail of histone H4.

The term "peptide" as used herein refers to short polymers formed from the linking, in a defined order, of α-amino acids. The link between one amino acid residue and the next is known as an amide bond or a peptide bond. Proteins are polypeptide molecules (or consist of multiple polypeptide subunits). The distinction is that peptides are short, and polypeptides/proteins are long. There are several different conventions to determine these. Peptide chains that are short enough to be made synthetically from the constituent amino acids are called peptides, rather than proteins, with one commonly understood dividing line at about 50 amino acids in length. In some embodiments, the peptides are from the N-terminal tails of Histones H2A, H2B, H3 or H4. In some embodiments, the peptides are from the N-terminal tail of Histone H4. Exemplary peptides include, but are not limited to, Histone H4-21, Histone H4-16, Histone H4-13, and Histone H4-8. In some embodiments the Histone H4-16 peptide is used as the template for construction of the peptide mimetic.

The term "peptide mimetic" as used herein refers to a small molecule that biologically mimics a natural peptide by retaining the ability of the peptide to interact with a biological target and produce the same biological effect. The molecule includes, but is not limited to, a synthetic peptide, a peptoid, a modified peptide, a β-peptide or any other molecule that biologically mimics a natural peptide. The peptide mimetic may have improved stability and/or pharmacokinetic properties, such as bioavailability, receptor selectivity, and potency, compared to the natural peptide. In some embodiments, the peptide mimetic is a peptoid.

The term "peptoid" as used herein refers to a peptide mimetic with N-substituted glycine polymers having the side chains appended to the backbone nitrogen as opposed to the α-carbon. In some embodiments, the peptoids are based on peptides from the N-terminal tail of Histone H4.

The term "warhead peptoid" as used herein refers to a haloacetamidine peptoid having the structure shown in FIG. 10 in which n is an integer from 1 to 4 and X is a halogen selected from chlorine (Cl), iodine (I), flourine (F), bromine (Br), astatine (At), or tennessine (Ts). In some embodiments, the warhead is a a chloracetamidine warhead. Peptoids of varying lengths and monomer units may incorporate a haloacetamidine warhead. In the structure of FIG. 10, $R_1$ and $R_2$ may be comprised of one or more of the same or varying amine monomers (i.e. N-substituted glycine polymers), such as those shown in FIG. 2. As used herein, "amine monomer" and "N-substituted glycines" are used interchangeably.

The term "monomer" as used herein refers to small molecules bonding together to form more complex structures such as proteins or peptides. In particular, the term "monomer" as used herein refers to amine monomers, i.e. N-substituted glycines. Any compound with a free amine can be used to make a peptoid monomer.

As used herein, the phrase "natural amino acid" refers to the any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group.

As used herein, the phrase "unnatural amino acid" refers to amino acids not included in the list of 20 amino acids naturally occurring in proteins, as described above. Such amino acids include the D-isomer of any of the 20 naturally occurring amino acids. Unnatural amino acids also include homoserine, ornithine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labeled, and the like.

As used herein, the term "pharmaceutically acceptable carrier" is used to describe any of the standard pharmaceutically acceptable carriers. The pharmaceutically acceptable carrier can include excipients such as diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19$^{th}$ ed.) describes formulations which can be used in connection with the subject invention.

Any of the compounds disclosed herein may be administered with or without an excipient. Excipients include, for example, encapsulating materials or additives such as absorption accelerators; antioxidants; binders; buffers; coating agents; coloring agents; diluents; disintegrating agents; emulsifiers; extenders; fillers; flavoring agents; humectants; lubricants; perfumes; preservatives; propellants; releasing agents; sterilizing agents; sweeteners; solubilizers; wetting agents; and mixtures thereof.

The term "compound" as used herein refers to a chemical formulation, either organic or inorganic, that induces a desired pharmacological and/or physiological effect on a subject when administered in a therapeutically effective amount. "Compound" is used interchangeably herein with "drug" and "therapeutic agent". A compound may include pharmaceutically acceptable salts, prodrugs, salts of a prodrugs and metabolites thereof.

"Treatment" or "treating" as used herein refers to any of: the alleviation, amelioration, elimination and/or stabilization of a symptom or characteristic, as well as delay in progression of a symptom of a particular disorder, such as a PRMT-associated disorder. For example, "treatment" of a PRMT-associated disorder may include any one or more of the following: amelioration and/or elimination of one or more symptoms/characteristics associated with the PRMT-associated disorder, reduction of one or more symptoms/characteristics of the PRMT-associated disorder, stabilization of symptoms/characteristics of the PRMT-associated disorder, and delay in progression of one or more symptoms/characteristics of the PRMT-associated disorder.

As used herein, the term "therapeutically effective amount" is determined based on such considerations as known in the art including the recipient of the treatment, the recipient's tolerance for the compound, the disorder being treated, the severity of the disorder being treated, the composition containing the compound, the time of administration, the route of administration, the duration of treatment, the potency of the compound, the bioavailability of the compound, the rate of clearance of the compound from the body, and whether or not another active agent is co-administered. The amount of the compound of the instant invention that may be administered to a subject must be effective to achieve a response, including but not limited to, improved survival rate, more rapid recovery, and improvement or elimination of symptoms associated with cancers. In accordance with the present invention, a suitable single dose size is a dose that is capable of preventing or alleviating (reducing or eliminating) a symptom in a patient when administered one or more times over a suitable time period. One of ordinary skill in the art can readily determine appropriate single dose sizes for systemic administration based on the size of a mammal and the route of administration.

As used herein, "administering" or "administration" refers to the process by which the compounds of the present invention are delivered to a subject. The compounds of the present invention may be administered in a variety of ways including, but not limited to, buccally, opthalmically, orally, osmotically, parenterally (intramuscularly, intraperitoneally, intrasternally, intravenously, subcutaneously), rectally, topically, transdermally, or vaginally. Any of the compounds may also be delivered through encapsulation in vesicles such as liposomes, niosomes, micelles, etc.

As used herein, an "active agent" refers to a composition, compound, chemical, extract or substance that has measurable specified or selected physiologic activity when administered to a subject in a therapeutically effective amount. In some embodiments, the active agent is an inhibitor of PRMT. In other embodiments, the active agent is an agent that can be administered with a an inhibitor of PRMT disclosed herein to the alleviate, ameliorate, eliminate and/or stabilize a given symptom or characteristic, as well as delay progression of a symptom of a PRMT-associated disorder.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds used in other embodiments of the present invention. Additionally, compounds used in the present invention may be administered in combination with or concurrently with other therapeutics for PRMT-associated disorders.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms.

Peptides have been used in traditional enzymatic assays, high-throughput screening methodologies, and mass spectrometry platforms to determine the catalytic mechanism and substrate specificity of the PRMT isozymes as well as scaffolds for chemical probes and inhibitors. These studies have provided important information regarding amino acid sequences and modifications necessary for targeting specific PRMT isozymes [17,28,44]. Such information about specificity is crucial for developing novel pharmaceuticals that target particular isozymes. However, the in vivo utility of peptides is severely limited by rapid degradation through proteolysis thus limiting their therapeutic potential.

Peptoids offer an important alternative as this minor change to the backbone structure maintains many key structural characteristics that are necessary for protein-substrate binding, while increasing the lifetime of the product in vivo. Thus, the kinetic parameters of the peptide substrate versus the peptoid substrate would be expected to be fairly similar, and the resulting peptoid-scaffold could be further elaborated into specific inhibitors and chemical probes, providing the community with more useful in vivo tools.

The present disclosure provides peptide mimetics, such as peptoids, and methods of treating PRMT-related disorders. The following non-limiting examples illustrate exemplary compounds, compositions, and methods of treatment thereof in accordance with various embodiments of the disclosure. The examples are merely illustrative and are not intended to limit the disclosure in any way.

Example 1—Peptoids Mimicking PRMT-Peptide Substrates

PRMT family members are categorized as histone-modifying enzymes and catalyze the methylation of arginine residues within the N-terminal tails of Histones H2A, H2B, H3, and H4. Arg3 on Histone H4 is primarily modified by PRMT1 or PRMT5, which are responsible for nearly 90% of all arginine methylation in mammals [45,46]. Previous studies have evaluated and reported the kinetic parameters of peptides based on the H4 N-terminal tail [10,47]. The kinetic parameters of these peptides, such as AcH4-21, with PRMT1 have shown $k_{cat}$ and $K_m$ values that are similar to those of native histones [10]. However, AcH4-21 has three arginine residues in the peptide located at R3, R17, and R19.

These multiple arginine residues complicate analysis, thus the inventors focused on the AcH4-16 peptide.

Synthesis of Peptoids Mimicking PRMT-Peptide Substrates

Figure 2:
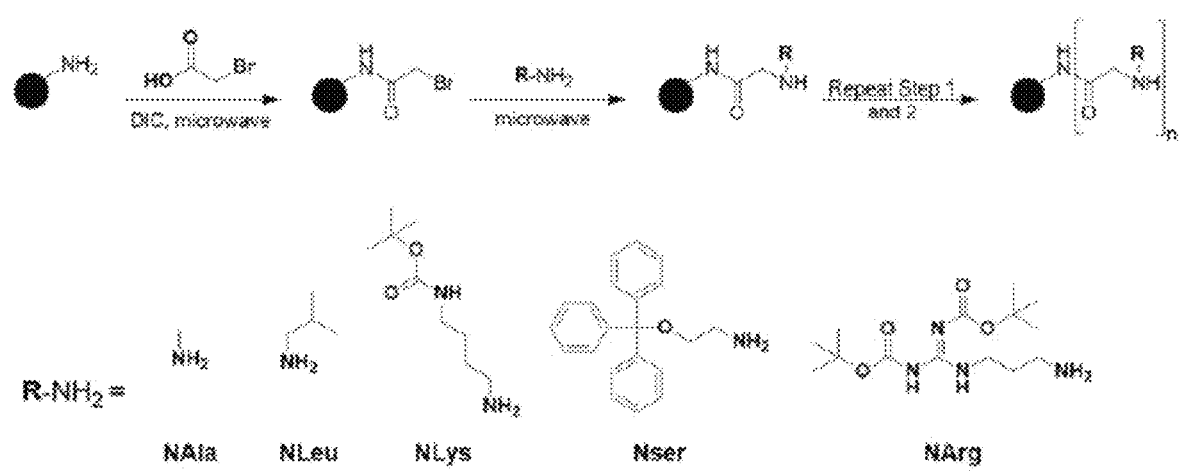
FIG. 2 is an image depicting the synthesis of peptoids with monomer units. The protecting groups on the amine monomers are shown in grey.
Figure 3:
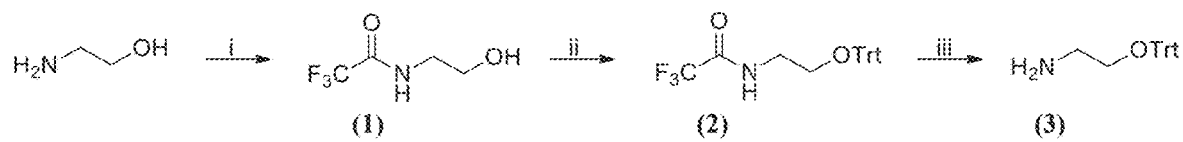
FIG. 3 is an image depicting Synthesis of 2-(Triphenylmethoxy)ethanamine: i) trifluoro acetate; ii) trityl chloride, diisopropylethylamine, DCM; iii) NaOH, MeOH. Synthesis of 2-(Triphenylmethoxy)ethanamine: Ethyl trifluoroacetate (2.26 mL, 19 mmol) was cooled to 0° C. and ethanolamine (0.85 mL, 14 mmol) was added dropwise, and the mixture was allowed to warm to rt. After 2 h, the volatiles were removed under reduced pressure to afford the amide product (1) (1.98 g, 12.6 mmol) in 90% yield. $^1$H NMR ($D_2O$): 3.58 (t, 2H, J=5.38), 3.33 (t, 2H, J=5.38); $^{13}$C NMR ($D_2O$): 161.69 (q, J=37), 118.37 (q, J=283.8), 61.74, 44.30. N-(2-hydroxyethyl)-2,2,2-trifluoroacetamide (1) (1.63 g, 10.3 mmol) was dissolved in DCM (20 mL) and cooled to 0° C. Trityl chloride (3.47 g, 12.5 mmol) and diisopropylethylamine (2.22 mL, 12.5 mmol) were added slowly and the reaction was allowed to warm to rt over 5 h. The reaction was quenched with 5% acetic acid (20 mL) and the layers were separated and the aqueous phase was extracted twice with DCM (2×30 mL). The organics were combined, washed with saturated sodium bicarbonate (20 mL) and brine (20 mL), dried over magnesium sulfate, and concentrated under reduced pressure to afford the trityl protected product (2). $^1$H NMR ($CDCl_3$): 7.45 (m, 5H), 7.35 (M, 10H), 6.60 (br s, 1H), 3.54 (m, 2H), 3.33 (m, 2H). $^{13}$C ($CDCl_3$): 157.1 (q, J=37), 143.4, 128.5, 128.0, 127.4, 115.8 (q, J=286.5), 87.1, 61.4, 40.0.

The inventors previously showed that AcH4-16 is still a good substrate for PRMT1 with a $k_{cat}/K_m$ value of $1.90 \times 10^3 M^{-1} min^{-1}$ and simplifies the analysis because of a single arginine residue of R3 (Table 1) [7]. For this reason, the inventors chose to construct peptoids based on the H4-16 peptides using monomers that mimicked the side chain of amino acids found in the peptide (FIG. 2). Many of the amine building blocks are readily available and synthetic methodologies have been well described in Zuckerman et al. and Olivos et al., both of which are incorporated in their entirety herein [34,48]. However, the synthesis of the N-serine peptoid monomer was adapted from previously developed protocols (FIG. 3).

TABLE 1

Kinetic parameters of selected peptides with PRMT1[1,2]

| Peptide | $K_{cat}$ (min$^{-1}$) | $K_m$ (µM) | $K_{cat}/K_m$ (M$^{-1}$ min$^{-1}$) |
|---|---|---|---|
| ACH4-21 | 0.44 ± 0.01 | 1.61 ± 0.11 | $2.80 \times 10^5$ |
| AcH4-18 | 0.32 ± 0.01 | 170 ± 25 | $1.90 \times 10^3$ |

[1]These values were reported in Nguyen et al. [7].
[2]The SAM concentration for determining these values was 15 µM.

Determining the Kinetic Parameters of Peptoids

Once the peptoids were synthesized and purified, the inventors evaluated the kinetic parameters of each peptoid using a standard methyltransferase assay to determine if the peptoid-scaffold contributed to any changes in the kinetic values compared with the peptides. In addition, the effects of N-terminal acetylation on substrate binding or catalysis were examined. Interestingly, the tested peptoids were not modified at any measurable rate, even at high substrate concentrations (>1000 µM). The kinetic parameters of the acetylated peptoids (AcH4-16, AcH4-13, and AcH4-8) could not be determined due to low product turnover. The role of N-terminal amino group was further examined by synthesizing unacetylated versions of H4-16, H4-13, and H4-8 (FIG. 4). Results of from these studies indicate that the unacetylated versions of these peptoids were slightly better substrates for PRMTs than their acetylated counterparts, but the $k_{cat}/K_m$ values were still extremely low (~$10^{-17}$ µM$^{-1}$ min$^{-1}$) demonstrating them as poor PRMT substrates overall (Table 2 and FIG. 5). Given that the structures of the peptides and peptoids are not very different, these peptide mimetics can act as inhibitors of PRMTs rather than substrates.

TABLE 2

Kinetic parameters of peptoids with PRMT1

| Peptoid | $K_{cat}$ (min$^{-1}$) | $K_m$ (µM) | $K_{cat}/K_m$ (M$^{-1}$ min$^{-1}$) |
|---|---|---|---|
| ACH4-16 | nd[1] | nd[1] | nd[1] |
| H4-16 | $1.9 \times 10^{-8} \pm 1.6 \times 10^{-6}$ | 316 ± 801 | $6.0 \times 10^{-17}$ |
| ACH4-13 | nd[1] | nd[1] | nd[1] |
| H4-13 | $3.4 \times 10^{-8} \pm 9.5 \times 10^{-8}$ | 516 ± 334 | $6.6 \times 10^{-17}$ |
| ACH4-8 | nd[1] | nd[1] | nd[1] |
| H4-8 | nd[1] | nd[1] | nd[1] |

[1]The kinetic parameters for these compounds were not determined due to a lack of product formation, SAM concentration was 40 µM.

Determining the Inhibition Properties of Peptoids

Given that kinetic analysis showed the peptoid mimetics to be poor substrates, the inventors sought to determine if the AcH4-16 peptoid could serve to inhibit PRMT1. An IC50 analysis of the AcH4-16 peptoid was measured against PRMT1, using the standard methyltransferase assay, demonstrated inhibition with a value of 916±19.5 µM, thus confirming that the peptoid versions were in fact inhibitors of PRMT1 (FIG. 6).

Because previous studies have indicated that residues distal from the active site are important for binding to PRMT1, the effect of overall peptoid length was investigated. The inhibitory effects of shorter peptoids based on the N-terminal tail of Histone H4, which included AcH4-13 and AcH4-8 were tested. The $IC_{50}$ values of AcH4-13 (FIG. 7A) and AcH4-8 (FIG. 8A) with PRMT1 were both determined to be >1000 µM, suggesting that the residues distal from the active site are important for binding to the enzyme.

Furthermore, the inventors evaluated the role of the N-terminus acetylation of the peptoids using the unacetylated version of H4-16. The $IC_{50}$ value of unacetylated H4-16 was measured as 396±31.4 µM (FIG. 9A), which was more than two-fold lower than the acetylated version of H4-16 and suggests that the positive charge at the N-terminus provides additional binding stabilization. Given this information, the inventors sought to determine if the truncated unacetylatedpeptoids, H4-13 and H4-8, showed a similar trend. The $IC_{50}$ value for unacetylated H4-13 was measured to be 898±93.5 µM, which was also less than its acetylated version (FIG. 7B). However, the unacetylated H4-8 did not show any inhibition up to 1000 µM (FIG. 8B; Table 3). This lack of inhibition was not surprising given the role of these distal residues on PRMT binding [10]. In total, these data suggest that PRMTs are inhibited by the histone peptoids and that the positively charged N-terminus favorably contributes to improved binding and inhibition.

TABLE 3

$IC_{50}$ values of peptoids with PRMT1[1]

| Peptoid | $IC_{50}$ (µM) |
|---|---|
| ACH4-16 | 916 ± 19.6 |
| H4-16 | 398 ± 31.4 |
| AcH4-13 | >1000 |
| H4-13 | 898 ± 93.5 |
| ACH4-8 | >1000 |
| H4-8 | >1000 |

[1]SAM concentration was 40 µM.

Determining the Inhibition Properties of Peptoids on PRMT5

The discovery of a peptoid-based inhibitors of PRMT1 is significant, but the selectivity of these inhibitors against other isozymes needed to be investigated. To this end, the best peptoid inhibitor, the unacetylated version of H4-16, was tested against PRMT5. As a Type II PRMT, PRMT5 is responsible for ~90% of all SDMA produced in cells.

Briefly, PRMT5 was incubated in the presence of H4-16 peptoid, then residual activity was measured using the standard methyltransferase assay. The H4-16 peptoids resulted in an $IC_{50}$ value of greater than 1000 µM for PRMT5, which was higher than the unacetylated or acetylated versions of H4-16 peptoid for PRMT1 (FIG. 9B). In total, both PRMT1 and PRMT5 can be inhibited using peptoids thus suggesting that peptoids can serve as a novel scaffold for the PRMT family of enzymes. Furthermore, the level of inhibition can be controlled by the substrate specificity of these isozymes and provide a new way to modulate their activity as selective-PRMT inhibitors.

The inventors identified that peptoids based on known peptide substrates of the PRMT family are poor substrates, but in fact, they are micromolar inhibitors for these enzymes. These newly identified peptoids provide a novel scaffold for inhibitor design targeting the PRMT family of enzymes. Peptoids provide additional in vivo stability and an extended half-life when compared with peptides, thus providing a potentially more stable pharmaceutical. Subsequent modulation of the side chains can provide specificity for targeting individual isozymes within the family, and can also produce inhibitors with lower $IC_{50}$ values.

Materials and Methods

Materials

Reagents for peptoid synthesis included methylamine, isobutylamine, bromoacetic acid, diisopropylcarbodiimide (DIC), N-methylmorophiline, triethylamine, acetic anhydride, trifluoroacetic acid (TFA), triisopropylsilane (TIS), diethylether, and piperidine were purchased from Sigma-Aldrich. Fmoc-Gly-OH, Hexafluorophosphate Benzotriazole Tetramethyl Uronium (HBTU), dimethylformamide (DMF), dichlormethane (DCM), and Fmoc-MBHA Rink Amide Resin were purchased from VWR. Other biochemical reagents were purchased from Fisher Scientific. Kinetics were determined using the MTase-Glo Methyltransferase assay kit from Promega. PRMT1 and PRMT5 were expressed and purified as previously described in Nguyen et al., the entirety of which is incorporated herein by reference [7].

Preparation of Peptoid Monomers

Tert-butyl N-{[(3-aminopropyl)amino]({[(tert-butoxy)carbonyl]amino})methylidene}carbamate and N-(tert-Butoxycarbonyl)-1,4-butanediamine were synthesized as previous reported [41,42]. 2-(Triphenylmethoxy)ethanamine synthesis was accomplished by modification of a previously reported protocol by Wang et al., the entirety of which is incorporated herein by reference [43]. Briefly, ethanolamine was converted to the trifluoroacetamide by reaction with ethyl trifluoroacetate. The addition of the trityl protective group was accomplished by reaction of the alcohol with triphenylchloromethane. Subsequent removal of the trifluoroacetyl group with methanoic hydroxide yielded the serine analog for use in peptoid synthesis (FIG. 3).

Peptoid Synthesis

Peptoids were synthesized on Fmoc-MBHA Rink Amide Resin (0.44 mmol/g). Initially, the Fmoc protecting group was removed with the addition of 20% piperidine in DMF (3 ml for 20 min, then 3 ml for 10 min). Coupling of the peptoid monomers involved incubating the resin in 1:1 solution of 1 M bromoacetic acid and 1 M DIC in DMF. It is important to note that the inventors found >99.8% DMF was essential for this step. The resin was microwaved six times in 5 s intervals, with shaking (15 s) and venting between intervals to prevent overheating. Afterwards, the reaction was incubated at r.t., with shaking, for 15 min, then washed with DMF (5 ml, five times). Subsequently, a 0.5 M solution of the appropriate peptoid monomer in DMF was added to the resin and microwaved six times in 5 s intervals, with shaking (15 s) between the intervals. Again, the reaction was incubated at r.t. for 15 min, then the resin was washed with DMF (5 ml, five times). The addition of glycine residues followed traditional Fmoc peptide synthesis. The resin was incubated with five equivalents of Fmoc-Gly-OH, five equivalents of HBTU and 5% N-methylmorophiline for 1 h at r.t. Subsequently, the resin was washed with DMF, and the Fmoc group was removed in 20% piperidine in DMF (3 ml for 10 min, twice).

Acetylation of the N-terminus was accomplished by incubating the resin in 1:6 acetylating solution (1:1 triethylamine:acetic anhydride in 1:1 DMF:DCM) for 1 h at r.t. Afterward, the resin was washed with 1:1 DMF:DCM (5 ml, five times) then DMF (5 ml, five times). Completed peptoids were cleaved from the resin in a cleavage cocktail of TFA, TIS, and water (95:2.5:2.5) for 1 h, precipitated with cold diethyl ether, and dissolved in water. The cleaved peptoids were purified by reversed-phase high-performance liquid chromatography using a Vydac Protein and Peptide column (218TP152022) and eluting with a linear gradient of water to acetonitrile (0-60% over 26 min) at a flow rate of 10 ml/min. Both solvents were modified with 0.05% TFA. The mass of each purified peptoid was confirmed using electrospray ionization (ESI) mass spectrometry (Table 4).

TABLE 4

Mass of Synthesized Peptoids

| Peptoid | Exp. Mass | Obs. Mass | % Yield |
|---|---|---|---|
| AcH4-16 | 1469.9 ($735.95^{M+2H}$) | 735.79 $^{(M+2H)}$ | 26.5 |
| H4-16 | 1427.9 ($714.95^{M+2H}$) | 714.80 $^{(M+2H)}$ | 29.2 |
| AcH4-13 | 1212 | 1213.85 | 40.1 |
| H4-13 | 1170 | 1171.71 | 32.1 |
| AcH4-8 | 800 | 801.54 | 35.5 |
| H4-8 | 758 | 759.50 | 55.2 |

$K_m$ Assay

The kinetics of each peptoid were determined using the MTase-Glo Methyltransferase assay kit to monitor the conversion of S-adenosylmethionine (SAM) to S-adenosylhomocysteine (SAH). Briefly, various concentrations (0-1000 µM) of the peptoid in assay buffer (20 mM Tris-HCl pH 8.0, 50 mM NaCl, 1 mM EDTA, 3 mM MgCl2, 0.1 mg/ml BSA, 1 mM DTT) were incubated at 37° C. After 10 min, 200 nM PRMT1 was added to initiate the reaction. The reaction proceeded for 10 min at 37° C. until quenched with the addition of 0.5% TFA (0.1% final concentration, 10 min, r.t.) followed by the addition of MTase-Glo Reagent to a final concentration of 1×. After 30 min incubating at r.t, MTase-Glo Detection Solution was added and incubated for 30 min at r.t. Immediately afterwards, the luminescence signal was read with a BioTek Synergy 2 Multi-Mode Microplate Reader. Luminescence signal was converted to product concentration using SAH standards (0-5 µM), following the above assay. The initial rates were fitted into equation (1) using GraFit version 7.03.

$$V = V_{max}[S]/(K_m + [S]) \tag{1}$$

$IC_{50}$ Assay

The efficacy of the peptoid inhibitors was probed using the MTase-Glo Methyltransferase assay kit. Various concentrations (0-1000 µM) of peptoid was incubated in assay buffer (20 mM Tris-HCl pH 8.0, 50 mM NaCl, 1 mM EDTA, 3 mM MgCl2, 0.1 mg/ml BSA, 1 mM DTT) at 37° C. for 10 min. Afterward, the inhibitor was allowed to interact with 200 nM PRMT1 for 15 min at 37° C. The reaction was catalyzed with 225 µM of AcH4-21 (a PRMT1 peptide substrate), continued for 15 min at 37° C., was quenched with the addition of 0.5% TFA (0.1% final concentration, 10 min, r.t.), followed by the addition of MTase-Glo Reagent to a final concentration of 1×. After 30-min incubation at r.t., MTase-Glo Detection Solution was added and incubated for 30 min at r.t. Luminescence signal was converted to product concentration using SAH standards (0-5 µM), following the above assay. Immediately afterwards, the luminescence signal was read with a BioTek Synergy 2 Multi-Mode Microplate Reader. IC50 values were determined by fitting the data to equation (2) using GraFit version 7.03.

Fractional activity of PRMT=1/(1+([I]/IC$_{50}$))  (2)

where [I] is the inhibitor concentration and IC$_{50}$ is the concentration of inhibitor resulting in 50% PRMT activity.

Example 2—Warhead Peptoids

As noted previously, PRMT family members catalyze the methylation of arginine residues in a variety of proteins, but have been extensively studied in relation to their modification of the N-terminal tail of histone proteins. The family of PRMTs have varying substrate specificity in regards to these histone tails. For example, PRMT1 and PRMT5 are primarily responsible for more than 90% of the methylation of Arg3 on Histone H4. Meanwhile, PRMT4 (CARM1) does not methylate H4R3, but is responsible for the majority of methylation found on Arg17 on Histone H3. These similarities and differences in substrate specificity provide an opportunity to design inhibitors targeting either single PRMTs or multiple family members. Peptides based on the N-terminal tail of these histones have been shown to have kinetic parameters, $k_{cat}$ and $K_m$, that are similar to those of native histones. Whereas peptoid mimics of these peptides are very poor PRMT substrates overall with $k_{cat}/K_m$ values ~10$^{-17}$M$^{-1}$ min$^{-1}$. Interestingly, these peptides based mimics of the histone N-terminal tail, H4-16 peptoids, are moderate inhibitors of PRMT1 with IC$_{50}$ values in the high µM range (~400-900 µM). Although the values are fairly high, they do provide a novel scaffold for inhibitor design targeting the PRMT family. Thus, the inventors utilized this scaffold to develop more specific and improved binding compounds specifically targeting PRMT1.

Synthesis of Warhead Peptides

Similar to the warhead peptoids described below, the inventors synthesized both unacetylated and acetylated warhead peptides (FIG. 11). The inventors conducted an IC$_{50}$ analysis of these compounds for PRMT1 using the standard methyltransferase assay. As shown in FIG. 12, the unacetylated H4-16 warhead peptide exhibited an IC$_{50}$ value of 29.5689±5.16 µM. The acetylated H4-16 warhead peptide exhibited an IC$_{50}$ value of 46.9426±4.86 µM. (FIG. 13).

Synthesis of Warhead Peptoids

Histone H4-16 peptoids have been shown to be moderate inhibitors of PRMT1 with some degree of selectivity over PRMT5. In addition, this peptoid contains only a single Arg residue, H4R3, in its sequence, which simplifies the analysis and can be used for the development of second-generation histone-based peptoid inhibitors. Modifying this single Arg residue to incorporate a reactive warhead would provide the ability to bind irreversibly to the PRMT1 active site and potentially lead to greater inhibition and selectivity. PRMT1 contains a Cys residue at 101 and is directly located in the active site, but is not conserved in other PRMT family members. Replacing H4R3 with a chloracetamidine warhead, a well-characterized Cys modifier, could lead to selective, irreversible modification of PRMT1. For this reason, the inventors chose to construct an H4-16 peptoid replacing Arg3 with a chloracetamidine warhead (FIG. 14). To determine if acetylation was important in regards to these peptoids, the inventors synthesized both an acetylated and unacetylated version of the H4-16 warhead peptoid (FIG. 15).

Determining the Inhibition Properties of the Warhead Peptoids

These peptoids would be expected to have improved potency and selectivity as compared to the H4-16 peptoids that lacked the ability to irreversibly modify PRMT1. To this end, the inventors conducted an IC$_{50}$ analysis of these compounds for PRMT1 using the standard methyltransferase assay, in addition to evaluating their ability to selectively target PRMT1 over PRMT5. PRMT1 was treated with the AcH4-16 warhead peptoid and resulted in an IC$_{50}$ value of 59.1±2.21 µM (FIG. 16), which is improved potency over the original AcH4-16 peptoid (15-fold). However, the unacetylated H4-16 warhead peptoid resulted in a IC$_{50}$ value of 8.73±0.314 µM with respect to PRMT1 (FIG. 17) which is a 45-fold increase in potency compared to the original unacetylated H4-16 peptoid. These data support previous studies that a positive charged N-terminus is favored by PRMT1 leading to increased binding and inhibition.

Furthermore, the inventors sought to determine if the Cl-warhead, which selectively modifies Cys residues, would provide further selectivity for PRMT1 over PRMT5. The IC$_{50}$ value for the AcH4-16 and unacetylated warhead peptoid with PRMT5 were determined to be >500 µM. (FIG. 18) The difference in IC$_{50}$ values between PRMT1 and PRMT5 was not surprising, but provides evidence that individual members of this family can be selectively targeted to develop peptoid-based inhibitors.

Effect of Unacetylated H4-16 Warhead Chloracetamidine Peptoid Inhibitor on Cell Viability To study the anticancer potential of the unacetylated H4-16 warhead chloracetamidine peptoid inhibitor, also referred to herein as PRMT inhibitor (P2), MDA468 breast carcinoma and HCT-116 colon carcinoma cells along with HepaRG immortalized, terminally differentiated liver cells were grown in the presence of various concentrations of the P2 compound (0-40 µM) for 48 hours and cell viability was assessed using crystal violet assay. P2 had significant antiproliferative affect in a dose-response manner on both cancer cells while no prominent change was seen in the viability of the non-tumorigenic HepaRG cells (p<0.01) (FIGS. 19A and B). The proliferation was reduced most significantly in MDA468 cells (55% at 20 µM and 75% at 40 µM). Although HCT-116 responded to the compound well, the effects were less pronounced with 40% reduction at 20 µM and 60% at the highest concentration (FIG. 19B).

Next, the inventors examined the specificity of P2 on cancer cells over 72 hour time course using a panel of cancer and normal cells. Once again, there was a dose and time-dependent decrease in cell viability in both cancer cell lines (FIGS. 20A and B) while the non-tumorigenic HepaRG and normal Human Mammary Epithelial Cells (HMEC) showed no detectable effect in growth (FIGS. 20C and D). These results suggest the P2 compound specifically targets cancer cells and reduces their viability and growth potential without significant toxicity to normal and non-tumorigenic cells.

Effect of P2 on Cell Cycle

The inventors then investigated the mechanism of action behind the reduced growth and viability. One possibility was arrest of cell cycle in cells post P2 treatment. HepaRG-FUCCI cells were used to follow the cell cycle in real time in the presence or absence of P2 in the media. Significant reduction of cells entering cell cycle was seen after 48 hours of P2 treatment indicating that new cell cycle was inhibited by the compound (FIGS. 21A and B). Similar numbers of cells were seen in G2/M phase however, both at 48 and 72 hours of P2 treatment (FIG. 21A-D). Western blot analysis confirmed reduced number of cells entering G1 and S phase with inhibition of Cyclin D and A respectively in HepaRG cells (FIG. 21E). Both MDA468 and HCT116 cells however, showed little change in Cyclin D or Cyclin A expression possibly indicating minimal effect on cell cycle of cancer cells (FIG. 21E).

P2 Induces Apoptosis and Autophagy in Cancer Cells

Since no significant changes in cell cycle were observed in any of the cell lines, the inventors next observed cells treated with P2 after staining for morphological changes in response to the drug. Untreated cells remained healthy and normal in appearance throughout experimental time frame while several cells in the treated samples showed membrane blebbing, rounding and presence of small vacuoles which could all indicate apoptosis (FIG. 22A). Furthermore, significant caspase-3 activity was seen in a dose response manner in MDA468 after 24 h and in HCT116 after 48 h of treatment with P2. In contrast, minimal activation of caspase-3 was seen in HepaRG cells and only at the highest dose (FIGS. 22B and C). Combined these results implicate apoptosis as a mechanism of action for P2's observed anticancer activity.

The inventors also examined if autophagy could also play a role in the reduced viability seen after P2 treatment as a large percentage of treated cells showed presence of vacuoles (FIG. 23A). To study this phenomena further, cell areas were measured using ImageJ analysis in images taken from stained slides. Results showed significant decrease in size of cells in both cancer cell lines post P2 treatment while HepaRG remained unchanged (FIG. 23B-D). The reduction in size of cells could also be an additional sign of active autophagy in these cells (FIGS. 23B and C). LC3 western confirmed activation of autophagy in all three cell lines in response to P2 treatment (FIG. 23E). Taken together, the results find both apoptosis and autophagy as important pathways activated by P2 to induce growth arrest and cell death in cancer cells.

Materials and Methods

Peptoid Synthesis

The synthesis of peptoids was completed on Fmoc-MBHA Rink Amide Resin (0.55 mmol/g). The resin was treated with 20% piperidine in DMF (5 mL for 15 min, twice) to remove the Fmoc-protecting group. Individual peptoid monomers were added by first incubating the resin with a 1:1 mixture of 1M bromoacetic acid and 1M diisopropylcarbodiimide (DIC) in DMF (2 mL) and microwaved for 30 seconds total (6×5 seconds at 100% power; venting and rocking for 30 seconds in between intervals). High purity (>99.8%) DMF is required for the coupling steps. The resin was washed with DMF (5×5 ml) to remove any residual reagents. The resin was then treated with a 0.5M solution of the peptoid monomer in DMF before microwaving for 30 seconds total (6×5 seconds at 100% power; venting and rocking for 30 seconds in between intervals) before being washed with 5×5 mL of DMF. This procedure was repeated for each monomer addition. Traditional Fmoc peptide synthesis was followed for the addition of glycine residues, 5 equivalents of Fmoc-Gly-OH, 5 equivalents of HBTU and 5% N-methylmorophiline were incubated for 10 min before being added to the resin and rocked for 1 hr at r.t. The resin was washed with DMF (5×5 mL) and treated with 20% piperidine in DMF (5 mL for 15 min, twice) to remove the Fmoc-protecting group.

For acetylated N-terminal peptoids, the completed peptoid on resin was incubated with a 1:6 acetylating solution (1:1 triethylamine:acetic anhydride in 1:1 DMF:DCM) for 1 h at r.t. with rocking. Finally, the resin was washed with a 1:1 mix of DMF:DCM (5×5 mL).

The resin was treated with 95% trifluoroacetic acid (TFA), 2.5% triisopropylsilane, and 2.5% water for 1 h to cleave the peptoid from the resin. The TFA was evaporated and the peptoid was precipitated with cold diethyl ether before being redissolved in water and purified by reverse-phase HPLC on a Vydac Protein and Peptide column. The mass of the peptoids were confirmed by electrospray ionization (ESI) mass spectrometry.

$IC_{50}$ Assay

The $IC_{50}$ value for the peptoid inhibitors were measured using the MTase-Glo Methyltransferase assay kit (Promega). The peptoid was incubated in assay buffer (20 mM Tris-HCl pH 8.0, 50 mM NaCl, 1 mM EDTA, 3 mM MgCl2, 0.1 mg/mL BSA, 1 mM DTT) and substrate (0-1000 µM) at either 37° C. (PRMT1) or 25° C. (PRMT5). After a pre-incubation of 10 minutes, 200 nM PRMT1 or PRMT5 was added to the assay before adding in the substrate, AcH4-21, at 225 µM. The reaction proceeded for 15 minutes before being quenched with 0.5% TFA (0.1% final concentration), vortexed, and incubated for an additional 10 minutes. To detect product formation, the MTase-Glo Reagent was added for 30 minutes at r.t., followed by addition of the MTase-Glo Detection solution for an additional 30 minutes. Finally, the luminescence signal was measured using a BioTek Synergy 2 Multi-Mode Microplate Reader. The values were converted to product concentration using a standard curve of S-adenosylhomocysteine (SAH; 0-5 µM). The $IC_{50}$ values were determined using equation 1 and fit to a curve using GraFit 7.03.

$$\text{Fractional activity of PRMT} = 1/(1+([I]/IC_{50})) \quad (2)$$

$IC_{50}$ is the concentration of inhibitor resulting in 50% PRMT activity and [I] is the inhibitor concentration.

Cell Culture and Conditions

MDA-MB-468 breast carcinoma cells (ATCC; HTB132), HCT116+/+p53 colon carcinoma cells were grown in DMEM supplemented in 5% FBS. HepaRG terminally differentiated liver cell line (Thermoscientific; HPRGC10) and HepaRG-Fucci cells were grown in Williams media supplemented with Glutamax and 5% FBS and normal Human Mammary Epithelial Cells (HMEC) (ATCC; PCS-600-010) were grown in Mammary epithelial basal medium (ATCC; PCS-600-030) supplemented with mammary epithelial cell growth kit (ATCC; PCS-600-040). Cells were recovered with 0.25% trypsin-EDTA, plated on cell culture treated plates and/or coverslips according to the experimental design and incubated overnight in 37° C. humidified CO2 incubator kept at 5% CO2 (800WJ; Thermoscientific). Cells were washed twice with sterile PBS before switching to serum free treatment media along with varying concentrations of the PRMT inhibitor compound (0-40 µM).

Morphology

Cells were grown on cover slips, stained using Diff-Quick kit and observed for markers of apoptosis and stress which included a stalled, multinucleated, apoptotic and normal morphology. In addition, the cell body and nuclear diameter, cell body areas and presence of vacuoles was noted using microscopy and Image J image analysis of 3 representative sections on each coverslip.

Digital Image Analysis (DA)

Digital images of coverslips were obtained under 20× and 40× objective lens magnification. Image J software was used to count cells and nuclei. In addition, software was calibrated using a stage micrometer image and then subsequently used to determine cell body & nuclear diameters and individual cell areas.

Crystal Violet Cytotoxicity Assay

Cell viability and growth was assessed using the crystal violet assay as described by Oliver et al., J Cell Sci, 1989). Briefly, cells from various control and pretreated conditions were seeded in 96-well plates in triplicate at a density of $5 \times 10^3$ and grown for 72 h in normal cell culture media typically used for each cell line. Cells were fixed at each time point with 100% methanol and stained with 1% crystal violet in 0.01M borate buffer (pH 8.9). Absorbance of dye eluted in 1:1 (v/v) ethanol: 0.01M HCl was checked at 650 nm by microplate reader. The cell growth rate was calculated by the following formula: Cell growth rate (%)=(A650 at n hour/A650 0 h). Each condition was tested in triplicate and repeated three independent times.

Fluorescent Microscopy for Cell Cycle

HepaRG-Fucci cells were grown in Williams media supplemented with Glutamax and 5% FBS and left untreated or treated with 10 or 40 uM PRMT inhibitor for 24-72 hours. Cells were visualized using Olympus fluorescent microscope, photographed and monitored for cell cycle activity by analyzing number of red (G1/S) and green (G2/M) cells.

Flow Cytometry for Cell Cycle 50,000 HepaRG cells were plated in duplicate for each time point for flow cytometry in 6 well plates. Cells were collected at the start of the treatment and at 24 At each time point, cells were harvested by trypsinization, collected using centrifugation at 2000 rpm, resuspended in ice cold PBS and fixed with 4.5 ml of 100% Methanol and stored at −20 until analysis. Cells were permeabilized using Triton-X and DNA within was stained with propidium iodide for 1 hour. Cells were then passed through a 0.45 μm filter to minimize cell clusters and aggregates. Doublets were excluded and 10,000 cells per sample were assessed by flow cytometry on a BD FACS Aria II flow cytometer using 100 μm nozzle at 20 psi. Fluorescence was used to estimated percent cells in G0/G1, S, or G2/M phase based on its relationship with DNA content.

Protein Extraction and Quantification

Cell lysates of cultured cells were prepared using the RIPA buffer supplemented with proteinase and phosphatase inhibitors. The samples were sonicated for 5 seconds on ice and centrifuged at 14000 rpm for 10 minutes 4° C. to remove debris. Samples were kept at −20° C. until use. The proteins were quantified using BCA protein assay against a BSA standard curve as per manufacturer's protocol (cat #23225, Thermo Scientific; IL, USA).

Caspase-3 Activity Assay

Caspase-3 activity assay was performed on extracted protein lysates using colorimetric caspase-3 activity assay (K106; Biovision) as per manufacturer's protocol. Briefly, 50 μL of extracted protein was plated in a UV compatible 96 well plate. DEVD-pNA substrate in prepared 1× buffer was added to each sample. The plate was shaken for 10 minutes and incubated at 37° C. in Biorad plate reader and read at 405 nm every 10 minutes for 2 hours. Raw caspase-activity was blank corrected and converted to relative caspase-3 activity compared to untreated control cells based on relative protein amount loaded in the assay.

Western Blotting

Expression of proteins was detected by Western blot assay as described previously. Briefly, cell extracts and tumor lysates were separated by SDS-PAGE followed by transfer to nitrocellulose membranes. Membranes were blocked with 5% milk in TBS-T (TBS containing Tween 20) for 30 min to 1 h and incubated in primary antibody (Santa Cruz, CA, USA) overnight at 4° C. followed by incubation in peroxidase-conjugated goat anti-rabbit IgG (1:500, Santa Cruz, CA, USA) for 1 h. Proteins were visualized by autoradiography and films were scanned. GAPDH was used as the loading control for western blotting with total liver protein extract. Ponceau staining of each protein column was also quantitated as an additional loading control for western blotting.

Antibodies and Reagents

Protease inhibitor cocktail (P8340), phosphatase inhibitor cocktail 2 (P5726) and 3 (P0044) and dimethyl sulfoxide (DMSO) (D8418) were purchased from Sigma-Aldrich (St. Louis, MO). The primary antibodies used in this study from Santa Cruz biotechnology were Cyclin D1 (sc-753); Cyclin A (sc-596); Cyclin B1 (sc-245). Additionally, the inventors used pHH3ser10 (9701A; Cell signaling, USA), LC-3 (L8918; Sigma) and GAPDH (IMG-5019A-2; Imgenex, Ca, USA). Horseradish Peroxidase-conjugated secondary antibodies of goat anti-rabbit (4010-05) and goat anti-mouse (1012-05) were purchased from Southern Biotech.

Data Analysis

Experimental data were expressed as average+/− Standard deviations. Significance for comparisons of two and multiple independent variables were calculated using Student's t-test and two-way ANOVA (PRISM software; Graphpad, CA USA), respectively. P value <0.05 was considered statistically significant.

Example 3 (Prophetic)

A 40 year old female patient is diagnosed with breast cancer. She is treated with a therapeutically effective amount of unacetylated H4-16 warhead chloracetamidine peptoid inhibitor over several weeks. After the treatment period, the number of breast cancer cells is reduced and the patient is found to be in remission.

Example 4 (Prophetic)

A 50 year old male patient is diagnosed with colon cancer. He is treated with a therapeutically effective amount of unacetylated H4-16 warhead chloracetamidine peptoid inhibitor over several weeks. After the treatment period, the number of colon cancer cells is reduced and symptoms improve. The patient is found to be in remission.

Conclusion

The inventors identified that peptoids based on known peptide substrates of the PRMT family are poor substrates, but in fact, they are micromolar inhibitors for these enzymes. These newly identified peptoids provide a novel scaffold for inhibitor design targeting the PRMT family of enzymes. Peptoids provide additional in vivo stability and an extended half-life when compared with peptides, thus providing a potentially more stable pharmaceutical. Subsequent modulation of the side chains can provide specificity for targeting individual isozymes within the family, and can also produce inhibitors with lower $IC_{50}$ values.

REFERENCES

[1] Lorton, B. and Shechter, D. (2019) Cellular consequences of arginine methylation. Cell. Mol. Life Sci. 76, 2933-2956

[2] Guccione, E. and Richard, S. (2019) The regulation, functions and clinical relevance of arginine methylation. Nat. Rev. Mol. Cell Biol. 20, 642-657

[3] Wolf, S. S. (2009) The protein arginine methyltransferase family: an update about function, new perspectives and the physiological role in humans. Cell. Mol. Life Sci. 66, 2109-2121

[4] Bedford, M. T. and Richard, S. (2005) Arginine methylation an emerging regulator of protein function. Mol. Cell 18, 263-272

[5] Di Lorenzo, A. and Bedford, M. T. (2011) Histone arginine methylation. FEBS Lett. 585, 2024-2031

[6] Zurita-Lopez, C. I., Sandberg, T., Kelly, R. and Clarke, S. G. (2012) Human protein arginine methyltransferase 7 (PRMT7) is a type III enzyme forming ω-NG-monomethylated arginine residues. J. Biol. Chem. 287, 7859-7870

[7] Nguyen, H. C., Wang, M., Salsburg, A. and Knuckley, B. (2015) Development of a plate-based screening assay to investigate the substrate specificity of the PRMT family of enzymes. ACS Comb. Sci. 17 500-505

[8] Nicklay, J. J, Shechter, D., Chitta, R. K, Garcia, B. A, Shabanowitz, J., Allis, C. D et al. Analysis of histones in *Xenopus laevis*. II. mass spectrometry reveals an index of cell type-specific modifications on H3 and H4. J. Biol. Chem. 2009; 284:1075-1085

[9] Okerberg, E. S., Wu, J., Zhang, B., Samii, B., Blackford, K., Winn, D. T. et al. (2005) High-resolution functional proteomics by active-site peptide profiling. Proc. Natl. Acad. Sci. U.S.A. 102, 4996-5001

[10] Osborne, T. C., Obianyo, O., Zhang, X., Cheng, X. and Thompson, P. R. (2007) Protein arginine methyltransferase 1: positively charged residues in substrate peptides distal to the site of methylation are important for substrate binding and catalysis. Biochemistry 46, 13370-13381

[11] Allali-Hassani, A., Wasney, G. A., Siarheyeva, A., Hajian, T., Arrowsmith, C. H. and Vedadi, M. (2012) Fluorescence-based methods for screening writers and readers of histone methyl marks. J. Biomol. Screen. 17, 71-84

[12] Wu, J., Xie, N., Feng, Y. and Zheng, Y. G. (2012) Scintillation proximity assay of arginine methylation. J. Biomol. Screen. 17, 237-244

[13] Prabhu, L., Chen, L., Wei, H., Demir, Ö., Safa, A., Zeng, L. et al. (2017) Development of an AlphaLISA high throughput technique to screen for small molecule inhibitors targeting protein arginine methyltransferases. Mol. Biosyst. 13, 2509-2520

[14] Musiani, D., Bok, J., Massignani, E., Wu, L., Tabaglio, T., Ippolito, M. et al. (2019) Proteomics profiling of arginine methylation defines PRMT5 substrate specificity. Sci. Signal. 12, eaat8388

[15] Hamey, J., Separovich, R. and Wilkins, M. (2018) MT-MAMS: protein methyltransferase motif analysis by mass spectrometry. J. Proteome Res. 17, 3485-3491

[16] Jain, K., Warmack, R., Debler, E., Hadjikyriacou, A., Stavropoulos, P. and Clarke, S. (2016) Protein arginine methyltransferase product specificity is mediated by distinct active-site architectures. J. Biol. Chem. 291, 18299-18308

[17] Gayatri, S., Cowles, M., Vemulapalli, V., Cheng, D., Sun, Z. and Bedford, M. (2016) Using oriented peptide array libraries to evaluate methylarginine-specific antibodies and arginine methyltransferase substrate motifs. Sci. Rep. 6, 28718

[18] Shishkova, E., Zeng, H., Liu, F., Kwiecien, N., Hebert, A., Coon, J. et al. (2017) Global mapping of CARM1 substrates defines enzyme specificity and substrate recognition. Nat. Commun. 8, 15571

[19] Mann, S., Salsburg, A., Causey, C. and Knuckley, B. (2019) The development and characterization of a chemical probe targeting PRMT1 over PRMT5. Bioorg. Med. Chem. 27, 224-229

[20] Lee, Y. H. and Stallcup, M. R. (2009) Minireview: protein arginine methylation of nonhistone proteins in transcriptional regulation. Mol. Endocrinol. 23, 425-433

[21] Pal, S. and Sif, S. (2007) Interplay between chromatin remodelers and protein arginine methyltransferases. J. Cell Physiol. 213, 306-315

[22] Pal, S., Baiocchi, R. A., Byrd, J. C., Grever, M. R., Jacob, S. T. and Sif, S. (2007) Low levels of miR-92b/96 induce PRMT5 translation and H3R8/H4R3 methylation in mantle cell lymphoma. EMBO J. 26, 3558-3569

[23] Chen, D., Ma, H., Hong, H., Koh, S. S., Huang, S. M., Schurter, B. T. et al. (1999) Regulation of transcription by a protein methyltransferase. Science 284, 2174-2177

[24] Herrmann, F., Pably, P., Eckerich, C., Bedford, M. T. and Fackelmayer, F. O. (2009) Human protein arginine methyltransferases in vivo-distinct properties of eight canonical members of the PRMT family. J. Cell Sci. 122(Pt 5), 667-677

[25] Zhao, X., Jankovic, V., Gural, A., Huang, G., Pardanani, A., Menendez, S. et al. (2008) Methylation of RUNX1 by PRMT1 abrogates SIN3A binding and potentiates its transcriptional activity. Genes Dev. 22, 640-653

[26] Dillon, M. B., Bachovchin, D. A., Brown, S. J., Finn, M. G., Rosen, H., Cravatt, B. F. et al. (2012) Novel inhibitors for PRMT1 discovered by high-throughput screening using activity-based fluorescence polarization. ACS Chem. Biol. 7, 1198-1204

[27] Obianyo, O., Causey, C. P., Jones, J. E. and Thompson, P. R. (2011) Activity-based protein profiling of protein arginine methyltransferase 1. ACS Chem. Biol. 6, 1127-1135

[28] Bicker, K. L., Obianyo, O., Rust, H. L. and Thompson, P. R. (2011) A combinatorial approach to characterize the substrate specificity of protein arginine methyltransferase 1. Mol. Biosyst. 7, 48-51

[29] Bergman S, H. and Comstock, L. (2015) N-mustard analogs of S-adenosyl-L-methionine as biochemical probes of protein arginine methylation. Bioorg. Med. Chem. 23, 5050-5055

[30] Vhuiyan, M., Thomas, D., Hossen, F. and Frankel, A. (2013) Targeting protein arginine N-methyltransferases with peptide-based inhibitors: opportunities and challenges. Future Med. Chem. 5, 2199-2206

[31] Zhang, J. and Zheng, Y. G. (2016) SAM/SAH analogs as versatile tools for SAM-dependent methyltransferases. ACS Chem. Biol. 11, 583-597

[32] de Freitas R, F., Ivanochko, D. and Schapira, M. (2019) Methyltransferase inhibitors: competing with, or exploiting the bound cofactor. Molecules 242019, 4492-4512

[33] Culf, A. and Ouellette, R. (2010) Solid-phase synthesis of N-substituted glycine oligomers (Alpha-Peptoids) and derivatives. Molecules (Basel, Switzerland) 15, 5282-5335

[34] Zuckermann, R. N., Kerr, J. M., Kent, S. B. H. and Moos, W. H. (2002) Efficient method for the preparation of peptoids [oligo(N-substituted glycines)] by submonomer solid-phase synthesis. J. Am. Chem. Soc. 114, 10646-7

[35] Cai, D., Lee, A., Chiang, C. and Kodadek, T. (2011) Peptoid ligands that bind selectively to phosphoproteins. Bioorg. Med. Chem. Lett. 21, 4960-4964

[36] Raveendra, B., Wu, H., Baccala, R., Reddy, M., Schilke, J., Bennett, J. et al. (2013) Discovery of peptoid ligands for anti-aquaporin 4 antibodies. Chem. Biol. 20, 351-359

[37] Lim, H.-S., Archer, C. T. and Kodadek, T. (2007) Identification of a peptoid inhibitor of the proteasome 19S regulatory particle. J. Am. Chem. Soc. 129, 7750-7751

[38] Corson, A., Armstrong, S., Wright, M., McClelland, E. and Bicker, K. (2016) Discovery and characterization of a peptoid with antifungal activity against *Cryptococcus neoformans*. ACS Med. Chem. Lett. 7, 1139-1144

[39] Levengood, M., Kerwood, C., Chatterjee, C. and van der Donk, W. (2020) Investigation of the substrate specificity of lacticin 481 synthetase by using nonproteinogenic amino acids. Chembiochem 10, 911-919

[40] Green, R. and Bicker, K. (2020) Evaluation of peptoid mimics of short, lipophilic peptide antimicrobials. Int. J. Antimicrob. Agents 56, 106048

[41] Hickey, S. M., Ashton, T. D., Khosa, S. K. and Pfeffer, F. M. (2012) An optimised synthesis of 2-[2,3-Bis(tert-butoxycarbonyl)guanidino]ethylamine. Synlett 23, 1779-1782

[42] Chadwick, J., Jones, M., Mercer, A., Stocks, P., Ward, S., Park, B. et al. (2010) Design, synthesis and antimalarial/anticancer evaluation of spermidine linked artemisinin conjugates designed to exploit polyamine transporters in *Plasmodium falciparum* and HL-60 cancer cell lines. Bioorg. Med. Chem. 18, 2586-2597

[43] Wang, F., Good, J., Rath, O., Kaan, H., Sutcliffe, O., Mackay, S. et al. (2012) Triphenylbutanamines: kinesin spindle protein inhibitors with in vivo antitumor activity. J. Med. Chem. 55, 1511-1525

[44] Wooderchak, W. L., Zang, T., Zhou, Z. S., Acuña, M., Tahara, S. M. and Hevel, J. M. (2008) Substrate profiling of PRMT1 reveals amino acid sequences that extend beyond the "RGG" paradigm. Biochemistry 47, 9456-9466

[45] Blanc, R. S. and Richard, S. (2017) Arginine methylation: the coming of age. Mol. Cell 65, 8-24

[46] Boriack-Sjodin, P. A. and Swinger, K. K. (2016) Protein methyltransferases: a distinct, diverse, and dynamic family of enzymes. Biochemistry 55, 1557-1569

[47] Wang, M., Xu, R. M. and Thompson, P. R. (2013) Substrate specificity, processivity, and kinetic mechanism of protein arginine methyltransferase 5. Biochemistry 52, 5430-5440

[48] Olivos, H., Alluri, P., Reddy, M., Salony, D. and Kodadek, T. (2002) Microwave-assisted solid-phase synthesis of peptoids. Org. Lett. 4, 4057-4059

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A compound for inhibiting protein arginine methyltransferase (PRMT) comprising:
   a peptide mimetic wherein the peptide mimetic is a peptoid-based inhibitor of PRMT comprising Formula (I)

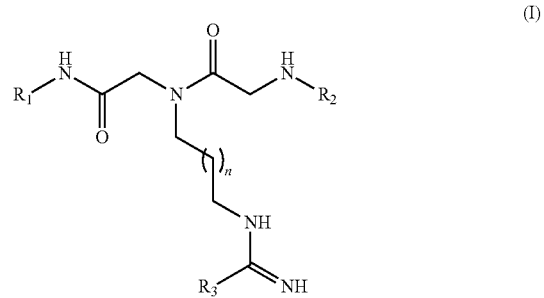

wherein $R_1$ is at least one amine monomer;
wherein $R_2$ is at least one amine monomer;
wherein $R_3$ is $NH_2$ or $CH_2$—X;
wherein X is a halogen; and
wherein n is an integer between 1 and 4.

2. The compound of claim 1, wherein $R_3$ is $CH_2$—X.

3. The compound of claim 1, wherein the peptoid-based inhibitor mimics an N-terminal tail of histone H4.

4. The compound of claim 3, wherein the peptoid-based inhibitor mimics Histone H4-16, Histone-H4-13, or Histone H4-8 peptide.

5. The compound of claim 1, wherein the peptoid-based inhibitor is unacetylated.

* * * * *